(12) United States Patent
Driehuys

(10) Patent No.: US 7,357,917 B2
(45) Date of Patent: *Apr. 15, 2008

(54) DIAGNOSTIC PROCEDURES USING $^{129}$XE SPECTROSCOPY CHARACTERSTIC CHEMICAL SHIFT TO DETECT PATHOLOGY IN VIVO

(75) Inventor: Bastiaan Driehuys, Chapel Hill, NC (US)

(73) Assignee: Medi-Physics, Inc., Princeton, NJ (US)

( * ) Notice: Subject to any disclaimer, the term of this patent is extended or adjusted under 35 U.S.C. 154(b) by 514 days.

This patent is subject to a terminal disclaimer.

(21) Appl. No.: 10/761,794

(22) Filed: Jan. 21, 2004

(65) Prior Publication Data

US 2004/0247526 A1   Dec. 9, 2004

Related U.S. Application Data

(63) Continuation of application No. 09/904,343, filed on Jul. 12, 2001, now Pat. No. 6,696,040.

(60) Provisional application No. 60/217,971, filed on Jul. 13, 2000.

(51) Int. Cl.
*A61B 5/055* (2006.01)

(52) U.S. Cl. .................. 424/9.3; 436/173; 600/410; 600/420

(58) Field of Classification Search ............... 424/9.3; 436/173; 600/410, 420
See application file for complete search history.

(56) References Cited

U.S. PATENT DOCUMENTS

| | | | |
|---|---|---|---|
| 5,545,396 A | 8/1996 | Albert et al. ............. 424/93 |
| 5,617,860 A | 4/1997 | Chupp et al. ............ 128/653.4 |
| 5,642,625 A | 7/1997 | Cates, Jr. et al. ........... 62/55.5 |
| 5,809,801 A | 9/1998 | Cates, Jr. et al. ............. 62/637 |
| 5,936,404 A | 8/1999 | Ladebeck et al. ........... 324/300 |
| 6,033,645 A | 3/2000 | Unger et al. ................ 424/9.5 |
| 6,051,208 A | 4/2000 | Johnson et al. ............. 424/9.3 |
| 6,079,213 A | 6/2000 | Driehuys et al. ............. 62/3.1 |
| 6,237,363 B1 | 5/2001 | Zollinger et al. ............. 62/600 |
| 6,338,836 B1 | 1/2002 | Kuth et al. ................. 424/9.3 |
| 6,370,415 B1 | 4/2002 | Weiler et al. .............. 600/410 |
| 2002/0006382 A1 | 1/2002 | Driehuys et al. |

FOREIGN PATENT DOCUMENTS

| | | |
|---|---|---|
| EP | 0933062 | 8/1999 |
| GB | 2091884 | 8/1982 |
| WO | WO 97/37239 | 10/1997 |
| WO | WO99/07415 | 11/1998 |
| WO | WO 99/25243 | 5/1999 |
| WO | WO99/47940 | 9/1999 |
| WO | WO 99/52428 | 10/1999 |
| WO | WO 99/53332 | 10/1999 |
| WO | WO 00/23797 | 4/2000 |
| WO | WO00/40972 | 7/2000 |
| WO | WO01/74246 | 10/2001 |
| WO | WO02/04709 | 1/2002 |

OTHER PUBLICATIONS

Albert et al., Measurement of $^{129}$Xe T1 in Blood to Explore the Feasibility of Hyperpolarized $^{129}$Xe.
MRI, Jour. Comp. Ass. Tomography, vol. 19, No. 6 (Nov.-Dec. 1995).
Bárány, M. et al., "High Resolution Proton Magnetic Resonance Spectroscopy of Human Brain and Liver," Magn. Reson. Imaging, 5:393 (1987).
Bifone, et al., "NMR of laser-polarized xenon in human blood," Proc. Natl. Acad. Sci. USA, vol. 93, pp. 12932-12936 (Nov. 1996).
Brookeman, J.R., "MRS and MRI of Hyperpolarized $^{129}$Xe: Studies in Human Volunteers," Proc. ISMRM (1998).
de Lange et al., "Lung Airspaces: MR Imaging Evaluation with Hyperpolarized Helium-3 Gas," Radiology 210, 851-857(1999).
Diehl et al., "Nuclear Magnetic Relaxation of the $^{129}$Xe and $^{131}$Xe Isotopes of Xenon Gas Dissolved in Isotropic and Anistropic Liquids," J. Magn. Reson., vol. 88, pp. 660-665 (1990).
Donnelly et al., "Cystic Fibrosis: Combined Hyperpolarized 3He-enhanced and Conventional Proton MR Imaging in the Lung—Preliminary Observations," Radiology 212 (Sep. 1999), 885-889 (1999).
Goodson et al., "In vivo NMR and MRI Using Injection Delivery of Laser-Polarized Xenon," 94 Proc. Natl. Acad. Sci. USA, pp. 14725-14729 (1997).
Grover, B.D., "Noble-Gas NMR Detection through Noble-Gas-Rubidium Hyperfine Contact Interaction," Phys. Rev. Lett., vol. 40, No. 6, pp. 391-392 (1978).
Hou, et al., "Optimization of Fast Acquisition Methods for Whole-Brain Relative Cerebral Blood Volume (rCBV) Mapping with Susceptibility Contrast Agents," J. Mag. Res. Imaging, vol. 9 pp. 233-239 (1999).

(Continued)

*Primary Examiner*—Michael G. Hartley
*Assistant Examiner*—Leah Schlientz
(74) *Attorney, Agent, or Firm*—Robert F. Chisholm

(57) ABSTRACT

An in vivo non-invasive method for detecting and/or diagnosing a pathological condition using hyperpolarized $^{129}$Xe spectroscopy is disclosed. Generally stated, the method includes determining the magnitude of spectral peaks which represent particular chemical shifts and comparing the observed magnitudes to those of healthy individuals. Preferably, the method includes subtracting substantial backgrounds and accounting for secondary conditions such as the polarization of hyperpolarized gas administered. Additionally, a quantitative analysis of hyperpolarized $^{129}$Xe spectra advantageously allows, a physician to establish the extent of disease progression. Advantageously, this method can be used regardless of the method of hyperpolarized $^{129}$Xe administration.

8 Claims, 15 Drawing Sheets

OTHER PUBLICATIONS

Il'yasov et al., "129Xe NMR in Study of Tissues and Plants," Appl. Magn. Reson. vol. 17, pp. 17-84 (1999).

Jameson et al., "Nuclear Spin Relaxation by Intermolecular Magnetic Dipole Coupling in the Gas Phase. 129Xe in Oxygen," J. Chem. Phys., vol. 89, p. 4074-4081 (1998).

Kaatz et al., "A comparison of molecular hyperpolarizabilities from gas and liquid," J. Chem. Phys., vol. 108, No. 3, pp. 849-856 (Jan. 15, 1998).

Kaiser, et al., "Diffusion and field-gradient effects in NMR Fourier spectroscopy," J. Chem. Phys., vol. 60, No. 8, pp. 2967-2979 (Apr. 15, 1974).

MacFall et al., "Human Lung Air Spaces: Potential for MR Imaging with Hyperpolarized He-$3^1$," Radiology, vol. 200, No. 2, pp. 553-558 (1996).

Mansfeld et al., "The use of $^{129}$Xe NMR exchange spectroscopy for probing the microstructure of porous materials," Chem. Phys. Ltrs., vol. 213, No. 1, 2, pp. 153-157 (Oct. 1, 1993).

Martin, "The Pharmacokinetics of Hyperpolarized Xenon: Implications for Cerebral MRI," Jour. Magn. Reson. Imag., vol. 7, No. 5, pp. 848-854 (Sep.-Oct. 1997).

McAdams et al., "Hyperpolarized 3He-Enhanced MR Imaging of Lung Transplant Recipients: Preliminary Results," AJR 173, 955-959 (1999).

Miller et al., "Xenon NMR: Chemical shifts of a general anesthetic common solvents, proteins, and membranes", Proc. of the Nat. Acad. of Sci. (USA), vol. 78, No. 8, pp. 4946-4949 (Aug. 1981).

Möller et. al., "Maganetic Resonance Angiography with Hyperpolarized 129Xe Dissolved in Lipid Emulsion," 41 Mag. Res. Med. No. 5, pp. 1058-1064 (1999).

Moschos, A. et al., "Communications Nuclear Magnetic Relaxation of Xenon-129 Dissolved in Organic Solvents," J. Mag. Reson., vol. 95, pp. 603-606 (1991).

Mugler, III et al., "MR Imaging and Spectroscopy Using Hyperpolarized 129Xe Gas: Preliminary Human Results," Magn. Reson. In Med., vol. 37, No. 6, pp. 809-815 (1997).

Patyal, "Longitudinal Relaxation and Diffusion Measurements Using Magnetic Resonance Signals from Laser-Hyperpolarized $^{129}$Xe Nuclei," J. Magn. Reson., vol. 126, No. 1, pp. 58-65, May 1997.

Pietraβ et al., "Optically Polarized 129Xe in NMR Spectroscopy," Advanced Materials, pp. 826-838 (1995).

Raftery, et al. , "High-Field NMR of Adsorbed Xenon Polarized by Laser Pumping," Phys. Rev. Lett., vol. 66, No. 5, pp. 584-587 (Feb. 4, 1991).

Rosen et al., Polarized $^{129}$Xe optical pumping/spin exchange and delivery system for magnetic resonance spectroscopy and imaging studies, Rev. Sci. Instrum., vol. 70, No. 2, pp. 1546-1552 (Feb. 1999).

Ruppert et al., "NMR of hyperpolarized $^{129}$Xe in the canine chest: spectral dynamics during a breath-hold," NMR Biomed., vol. 13, pp. 220-228 (2000).

Schoenborn, "Binding of Xenon to Horse Haemoglobin," Nature, vol. 208, pp. 760-762 (Nov. 20, 1965).

Swanson et al., "Brain MRI with Laser-Polarized $^{129}$Xe," Mag. Res. Med., vol. 38, pp. 695-698 (1997).

Tilton, Jr., et al, "Nuclear Magnetic Resonance Studies of Xenon-129 with Myoglobin and Hemoglobin," Biochemistry, vol. 21, No. 26, pp. 6850-6857 (1982).

Tseng et al., "NMR of Laser-Polarized $^{129}$Xe in Blood Foam," J. Mag. Res., vol. 126, pp. 79-86 (1997).

Wolber et al., "Spin-lattice relaxation of laser-polarized xenon in human blood," 96 Proc. Natl. Acad. Sci. USA, pp. 3664-3669 (Mar. 1999).

Wolber et al. "In vivo hyperpolarized $^{129}$Xe spectroscopy in tumors," Proc. Int'l. Mag. Reson. Med. 8, 1440 (2000).

Wolber et al. "In vivo hyperpolarized $^{129}$Xe spectroscopy in tumors" Mag. Reson. Med. 46, pp. 586-591 (2001).

Albert, et.al., "Susceptibility Changes Following Bolus Injections", Appendix B reprint from Magnetic Resonance in Medicine 29 700-708 (1993).

Belliveau et.al., Functional Cerebral Imagining by susceptibility-Contrast NMR, dated Dec. 7, 1989; Magnetic Resonance in Medicine 14, 538-546 (1990).

Chupp, et.al., "Chemical Shift Imaging of Laser-Polarized $^{129}$XE Magnetization in Rats In Vivo", European Radiology 9:B45 (1999).

Driehuys, et.al., "Surface Relaxation mechanisms of Laser-Polarized $^{129}$XE", Physical Review Letters vol. 74, No. 24, p. 4943-4946, dated Jun. 12, 1995.

Luhmer, et.al., "Study of Xenon Binding Cryptophane-A Using Laser-Induced NMR Polarization Enhancement", J. Am. Chem. Soc. Mar. 30, 1999, 121, 3502-3512.

Mazitov, et.al., "NMR Spectroscopy of 129Xe Dissolved in Tissues of Animals and Plants in vitro: Effect of Tissue with Cancer" Doklady Biophysics vols. 364-366, 1999.

Yablonskiy et.al., "Quantitative in vivo assessment of lung microstructure at the alvcolar level with hyperpolarized 3He diffusion MRI" www.pnas.org/cgi/doi/10.1073/pnas.05294699, PNAS, Mar. 5, 2002, vol. 99, No. 5, 3111-3116.

DIAGNOSTIC PROCEDURES USING $^{129}$XE SPECTROSCOPY CHARACTERSTIC CHEMICAL SHIFT TO DETECT PATHOLOGY IN VIVO

RELATED APPLICATIONS

This application claims the benefit of priority of U.S. Provisional Patent Application Ser. No. 60/217,971, filed 13 Jul. 2000, the contents of which are hereby incorporated by reference as if recited in full herein.

This application is a continuation of U.S. application Ser. No. 09/904,343 filed Jul. 12, 2001, which claims priority to U.S. Provisional application No. 60/217,971 filed Jul. 13, 2000, the entire disclosure which is hereby incorporated by reference herein as if having been fully disclosed herein.

FIELD OF THE INVENTION

The present invention relates to magnetic resonance spectroscopy methods utilizing chemical shifts of hyperpolarized $^{129}$Xe.

BACKGROUND OF THE INVENTION

MRI using hyperpolarized noble gases has been demonstrated as a viable imaging modality. See e.g., U.S. Pat. No. 5,545,396 to Albert et al. The contents of this patent are hereby incorporated by reference as if recited in full herein. Albert et al. proposed several techniques of introducing the hyperpolarized gas (either alone or in combination with another substance) to a subject, such as via direct injection, intravenous injection, and inhalation. See also "Biological magnetic resonance imaging using laser-polarized $^{129}$Xe," Nature, pp. 199-201 (Jul. 21, 1994). Other researchers have since obtained relatively high-quality images of the lung using pulmonary ventilation of the lung with both hyperpolarized $^3$He and $^{129}$Xe. See J. R. MacFall et al., "*Human lung air spaces. Potential for MR imaging with hyperpolarized He-3,*" Radiology 200, 553-558 (1996); and Mugler et al., "*MR Imaging and spectroscopy using hyperpolarized $^{129}$Xe gas: Preliminary human results*" Mag Res Med 37, 809-815 (1997). See also E. E. de Lange et al, "*Lung Airspaces. MR Imaging evaluation with hyperpolarized Helium-3 gas,*" Radiology 210, 851-857 (1999); L. F. Donnelly et al., "*Cysticfibrosis: combined hyperpolarized $^3$He-enhanced and conventional proton MR imaging in the lung—preliminary observations,*" Radiology 212, 885-889 (1999); and H. P. McAdams et al., "*Hyperpolarized $^3$He-enhanced MR imaging of lung transplant recipients: Preliminary results,*" AJR 173, 955-959 (1999).

These researchers and others have investigated vascular and tissue imaging using inhaled or injected hyperpolarized gases to observe and detect abnormalities in body cavities. $^{129}$Xe may additionally be used to detect abnormalities within tissues because of its high solubility (relative to He) and lipophilic nature. Despite these advantages, hyperpolarized $^{129}$Xe cannot readily or typically achieve the signal strength readily attainable with hyperpolarized $^3$He. Hyperpolarized $^{129}$Xe has an inherently shorter lifespan even under the best of conditions due to depolarizing interactions between $^{129}$Xe nuclei. When hyperpolarized $^{129}$Xe additionally interacts with body tissues, its lifetime is reduced further as will be discussed hereinbelow.

$^{129}$Xe can be administered to a patient by several means, such as by inhalation and injection. During inhalation delivery, a quantity of hyperpolarized $^{129}$Xe is inhaled by a subject (a subject breathes in the $^{129}$Xe gas) and the subject then holds his or her breath for a short period of time, i.e. a "breath-hold" delivery. This inhaled $^{129}$Xe gas volume then exits the lung space and is generally taken up by the pulmonary vessels and associated blood or pulmonary vasculature at a rate of approximately 0.3% per second. For example, for an inhaled quantity of about 1 liter of hyperpolarized $^{129}$Xe, an estimated uptake into the body is about 3 cubic centimeters per second or a total quantity of about 40 cubic centimeters of $^{129}$Xe over about a 15 second breath-hold period. Accordingly, it has been noted that such uptake can be used to generate images of pulmonary vasculature or even organ systems more distant from the lungs. See co-pending and co-assigned U.S. patent application Ser. No. 09/271,476 to Driehuys et al., entitled "Methods for Imaging Pulmonary and Cardiac Vasculature and Evaluating Blood Flow Using Dissolved Polarized $^{129}$Xe," the contents of which are hereby incorporated by reference as if recited in full herein.

Many researchers are also interested in the possibility of using inhaled $^{129}$Xe for imaging white matter perfusion in the brain, renal perfusion, and the like. While inhaled delivery $^{129}$Xe methods are suitable, and indeed, preferable, for many MR applications for several reasons such as the relatively non-invasive characteristics attendant with such a delivery to a human subject, inhalation or ventilation-based deliveries may not be the most efficient method to deliver a sufficiently large dose to more distant (away from the pulmonary vasculature) target areas of interest. In addition, due to the dilution of the inhaled $^{129}$Xe along the perfusion delivery path, relatively large quantities of the hyperpolarized $^{129}$Xe are typically inhaled in order to deliver a small fraction of the gas to the more distal target sites or organ systems. For example, the brain typically receives only about 13% of the total blood flow in the human body. Thus, the estimated 40 cc's of hyperpolarized $^{129}$Xe taken up into the pulmonary vessels from the 1-liter inhalation dose may be reduced to only about 5 cc's by the time it reaches the brain.

Further, the hyperpolarized state of the gas is sensitive and can decay relatively quickly due to a number of relaxation mechanisms. Indeed, the relaxation time (generally represented by a decay constant "To") of the $^{129}$Xe in the blood, absent other external depolarizing factors, is estimated at $T_1$=4.0 seconds for venous blood and $T_1$=6.4 seconds for arterial blood at a magnetic field strength of about 1.5 Tesla. See Wolber et al., Proc Natl Acad Sci USA 96:3664-3669 (1999). The more oxygenated arterial blood provides increased polarization life over the relatively de-oxygenated venous blood. Therefore, for about a 5-second transit time, the time estimate for the hyperpolarized $^{129}$Xe to travel to the brain from the pulmonary vessels, the $^{129}$Xe polarization is reduced to about 37% of its original value. In addition, the relaxation time of the polarized $^{129}$Xe in the lung itself is typically about 20-25 seconds due to the presence of paramagnetic oxygen. Accordingly, $^{129}$Xe taken up by the blood in the latter portion of the breath-hold cycle can decay to about 50% of the starting polarization (the polarization level of the gas at the initial portion of the breath-hold cycle). Thus, generally stated, the average polarization of the $^{129}$Xe entering the pulmonary blood can be estimated to be about 75% of the starting inhaled polarization value. Taking these scaling effects into account, the delivery to the brain of the inhaled $^{129}$Xe can be estimated as about 1.4 cc's of the inhaled one liter dose of $^{129}$Xe polarized to the same polarization level as the inhaled gas (0.75×0.37×5 cc's). This dilution reduces signal delivery efficiency; i.e. for remote target areas (such as the brain), the quantity of delivered $^{129}$Xe signal is typically severely reduced to only about 0.14% of that of the inhaled $^{129}$Xe. Since MR imaging requires high signal strength to achieve a clinically useful spatial resolution in the resulting image, inhalation delivery may not produce clinically desirable images of distal or remote target organs or regions. However, much smaller quantities, for example on the order of approximately 0.01 cc's of $^{129}$Xe, polarized to about 10%, are sufficient to provide signal information for MR spectroscopy.

An alternative method for delivering hyperpolarized $^{129}$Xe is injection. $^{129}$Xe injection can be accomplished by suspending the hyperpolarized gas in a carrier or by direct gaseous injection. See international patent application PCT/US97/05166 to Pines et al, the contents of which are hereby incorporated by reference as if recited in full herein. In this application, Pines et al describes suitable injectable solutions in which to suspend hyperpolarized gases for in vivo use to effectively target regions or areas of the body. See also co-pending U.S. patent application Ser. No. 09/804,369 to Driehuys et al., entitled "Diagnostic Procedure Using Direct Injection of Gaseous Hyperpolarized $^{129}$Xe and Associated Systems and Products," the contents of which are hereby incorporated by reference as if recited in full herein. Generally stated, this patent application describes methods and an associated apparatus for injecting hyperpolarized $^{129}$Xe directly into the vasculature. The gas is preferably delivered such that the gas substantially dissolves into the vasculature proximate to the injection site or alternatively resides in the bloodstream for a period of time. As also discussed therein, surfactants may preferably additionally be added to facilitate the dissipation of injected bubbles.

Spectroscopy using hyperpolarized $^{129}$Xe is advantageous because of the documented sensitivity of $^{129}$Xe to its environment and the comparatively low levels of hyperpolarized $^{129}$Xe signal attainable (due to both environmental factors and the inherent properties of $^{129}$Xe compared to hyperpolarized $^{3}$He). By nature, spectroscopy requires a much smaller signal density because high spatial resolution is not required. Nonetheless, important information can be garnered from hyperpolarized $^{129}$Xe spectroscopy. Many researchers have investigated characteristic chemical shifts observed when hyperpolarized $^{129}$Xe comes into contact with different tissues, as seen in Table 1. As shown, large frequency shifts (on the order of 200 parts per million or "ppm") from free gas phase (referenced at 0 ppm) have been observed. This frequency shift is far greater than that observed with proton spectroscopy (generally stated, at most about 5 ppm). Therefore, spectroscopy is a modality which may be particularly suited to capitalize upon the behavior of hyperpolarized $^{129}$Xe.

TABLE 1

Characteristic shifts from free gaseous hyperpolarized $^{129}$Xe (referenced at 0 ppm) of hyperpolarized $^{129}$Xe when exposed to different tissues.

| Tissue | ppm | Reference |
|---|---|---|
| Water | 191.2 | Wilson 99 |
| Epicardial fat | 192 | Swanson 99 |
| Brain, lipid rich | 194 | Albert 99 |
| Brain tissue | 194.5 | Swanson 97 |
| Plasma | 195.6 | Wilson 99 |
| Brain | 198.0 | Wilson 99 |
| Lung parenchyma | 198.6 | Wilson 99 |
| Brain tissue | 199 | Swanson 99 |
| Kidney | 199.8 | Wilson 99 |

TABLE 1-continued

Characteristic shifts from free gaseous hyperpolarized $^{129}$Xe (referenced at 0 ppm) of hyperpolarized $^{129}$Xe when exposed to different tissues.

| Tissue | ppm | Reference |
|---|---|---|
| Brain - lipid poor | 201 | Albert 99 |
| Liver | 201.8 | Wilson 99 |
| T. Californica membrane | 209 | Miller 81 |
| RBC (oxygenated) | 213.0 | Wilson 99 |
| RBC (de-oxygenated) | 216.0 | Albert 99 |

All of the studies tabulated above involve healthy tissues. However, because $^{129}$Xe is so sensitive to its environment, characteristics of diseased states can also be sensed with $^{129}$Xe spectroscopy. For example, Wolber et al., in "In vivo hyperpolarized $^{129}$Xe spectroscopy in tumors," Proc Int'l Mag Reson Med 8, 1440 (2000), suspended hyperpolarized $^{129}$Xe in perfluorooctyl bromide (PFOB) or saline and injected it into subcutaneous tumors grown in rats. Because Wolber et al. suspended $^{129}$Xe in a carrier fluid, the resultant signal spectrum was likely tainted or influenced by the carrier fluid. For example, the signal from the $^{129}$Xe in the saline may have substantially obscured the peak of interest (i.e. the peak reflecting the $^{129}$Xe in the tumor tissue).

However, these experiments provided very little in the way of quantifiable information. Diseases of interest often cannot be diagnosed merely by the appearance of peaks denoting characteristic chemical shifts, since healthy tissues may also exhibit the same characteristics (e.g., some lipid is expected, but an excess or reduced amount of lipid may be problematic). In view of the foregoing, there remains a need for improved methods to determine the presence of certain diseases and/or pathological conditions as well as the extent or progression of the disease or condition and/or other quantitative information.

OBJECTS AND SUMMARY OF THE INVENTION

It is therefore an object of the present invention to detect and diagnose pathological conditions in vivo utilizing characteristic chemical shifts of hyperpolarized $^{129}$Xe.

It is an additional object of the present invention to provide a method for quantifying the extent of a pathological condition.

It is a further object of the present invention to provide a method for quantification of pathological states in vivo, in a manner which can decrease the impact of certain potentially data corrupting parameters such as variations in polarization and the volume of hyperpolarized gas administered to a subject.

It is another object of the present invention to filter or suppress undesirable background information from the spectroscopic signal associated with the hyperpolarized gas, thereby providing signal characteristics associated with a physiological or pathological phenomenon of interest in vivo.

One aspect of the present invention is directed toward a method for detecting pathology using hyperpolarized $^{129}$Xe spectroscopy. This method involves administering a bolus of hyperpolarized $^{129}$Xe to a patient and transmitting an RF pulse to a region of interest. An NMR RF excitation coil positioned proximate the region of interest can be used to transmit and receive the signal(s). In addition, localizing gradients can be applied as needed in the presence of the RF pulse as is well known to those of skill in the art. The response of the hyperpolarized gas to the RF pulse is received such that spectral peaks of interest can be identified and analyzed. The spectral peak may be further evaluated or quantified, and/or normalized. A pathological condition can then be detected on the basis of comparing the spectral peaks with a standard spectrum.

In certain embodiments, the polarization of the $^{129}$Xe prior to administration as well as the volume of gas administered can be accounted for. Alternatively, the spectral peak of interest can be normalized by another selected spectral peak, such as the dissolved phase-plasma peak or dissolved phase RBC (red blood cell) peak.

In certain embodiments, where the pathological condition is a degenerative disease, the stage or progression, remission, or remedial state of the disease can be determined by taking a signal of a dose of hyperpolarized gas administered to a subject in vivo (a) at a first time and (b) at a second subsequent time (such as at selected intervals and/or before and after treatments). As such, the methods of the present invention can be used to monitor the progression of a disease and the efficacy of a treatment regimen.

In embodiments of the present invention, $^{129}$Xe signal data associated with the interaction of $^{129}$Xe and non-targeted tissues can be filtered out by employing selected RF pulse sequences. For example, NMR signals can be filtered on the basis of one or more of $T_1$, $T_2$, $T_1\rho$, $T_2^*$, diffusion coefficient, and velocity (of the blood).

Another aspect of the present invention is directed toward a method of detecting atherosclerosis in the coronary arteries. This method involves administering a bolus of hyperpolarized $^{129}$Xe gas to a patient, delivering at least a portion of the administered hyperpolarized $^{129}$Xe gas to a region of interest, applying at least one resonant RF pulse sequence to the region of interest, acquiring and analyzing at least one NMR response signal (associated with the $^{129}$Xe), and determining the presence of atherosclerotic plaques on the basis of the analyzed response signal.

In certain embodiments, the method can also include taking a background spectrum of the heart (a spectrum of the polarized $^{129}$Xe in the blood of the chambers/vessels of the heart), which can be subtracted from the acquired signal spectra to accentuate or amplify the signal of the hyperpolarized $^{129}$Xe in the tissue (vessel wall, plaque, or other biosubstance or analyte of interest). The signal acquisitions can carried out responsive to a cardiac event and the flip angles of the excitation pulse(s) or pulse sequence(s) can be chosen such that they do not destroy all the polarization of the gas within the heart itself. Alternatively, signals of the carotid arteries may be used as indicators of the health of the coronary arteries, which can allows larger flip angles and therefore a better SNR (signal-to-noise ratio) over other regions.

Because of the comparatively low signal of $^{129}$Xe (compared to $^3$He) and its solubility in lipids, $^{129}$Xe spectroscopy may be particularly suitable for obtaining in vivo pathologic information on certain internal locations over $^{129}$Xe imaging. For example, because $^{129}$Xe is further sensitive to its environment, spectroscopy using $^{129}$Xe may be used as a sensitive probe for diseased states, such as evaluating in vivo an increased lipid content characteristic of arteriosclerosis or altered cells such as those characteristic of tumors, plaques or other abnormalities.

Embodiments of the present invention are therefore directed toward a method of non-invasively or minimally invasively probing tissues in vivo to detect pathological or abnormal conditions. The hypersensitivity of $^{129}$Xe to its environment, when used according to the methods of the present invention, can advantageously allow a physician or a program means to quantitatively and/or qualitatively assess the presence and/or extent of a diseased condition. The hyperpolarized gas can be administered via any desired method including, for example, inhalation and injection.

BRIEF DESCRIPTION OF THE DRAWINGS

FIG. 12A illustrates the signal obtained for healthy tissue and FIG. 12B illustrates the signal obtained for plaque.

FIG. 13A illustrates the signal obtained for healthy tissue and FIG. 13B illustrates the signal obtained for plaque.

DETAILED DESCRIPTION OF EMBODIMENTS OF THE INVENTION

Figure 1:
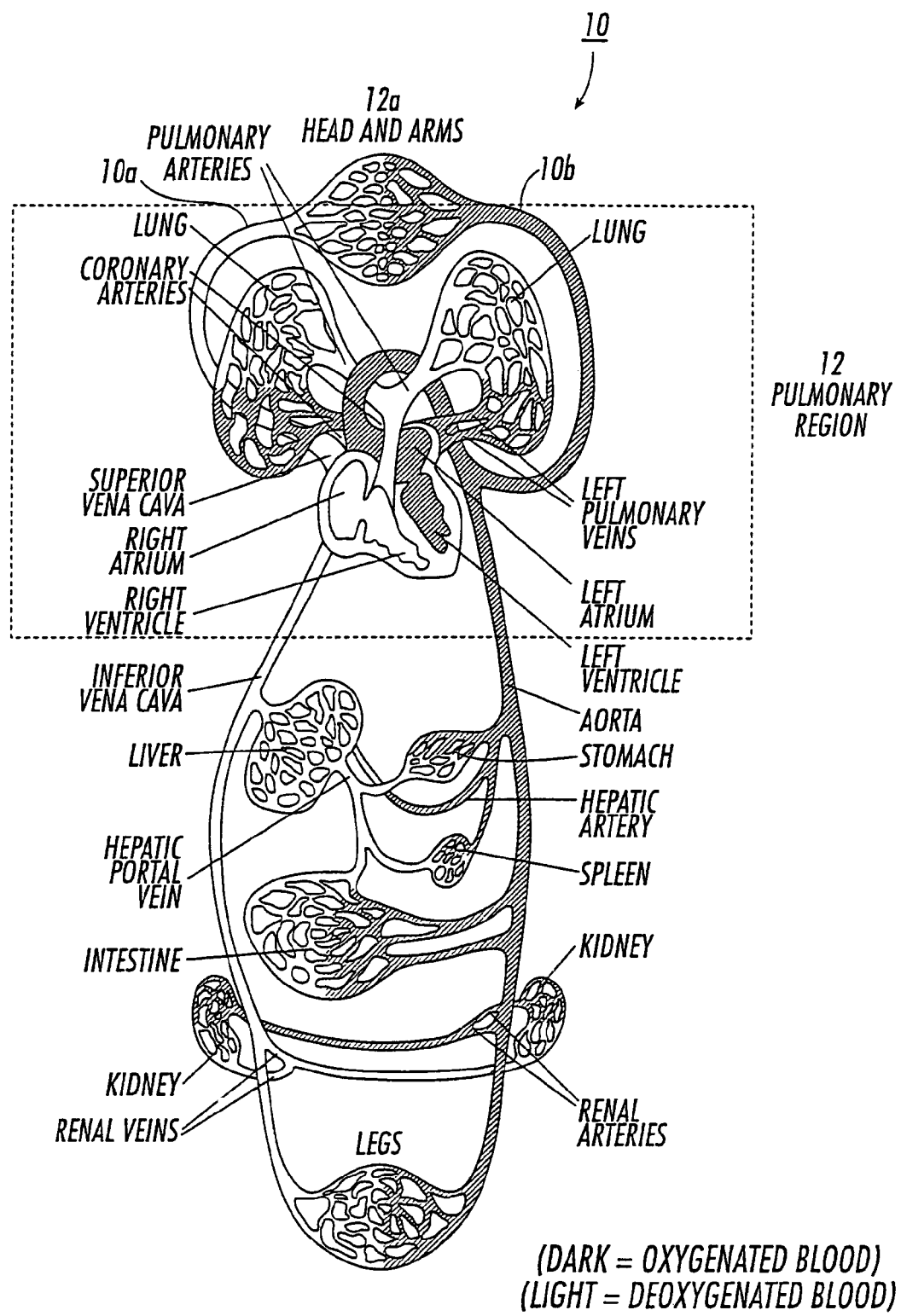
FIG. 1 is a schematic illustration of the human circulatory system illustrating the venous and arterial portions thereof. The deoxygenated blood is represented by the lighter/white regions and the oxygenated blood is represented by the darkened regions.

The present invention will now be described more fully hereinafter with reference to the accompanying drawings, in which preferred embodiments of the invention are shown. This invention may, however, be embodied in many different forms and should not be construed as limited to the embodiments set forth herein; rather these embodiments are provided so that this disclosure will be thorough and complete, and will fully convey the scope of the invention to those skilled in the art. Like numbers refer to like elements throughout. In the figures, certain layers, regions, features or components may be exaggerated or enlarged for clarity.

As known to those of skill in the art, polarized gases are collected, frozen, thawed, and used in MRI applications. For ease of description, the term "frozen polarized gas" means that the polarized gas has been frozen into a solid state. The term "liquid polarized gas" means that the polarized gas has been or is being liquefied into a liquid state. The term "gaseous hyperpolarized $^{129}$Xe" indicates the gaseous phase of the "hyperpolarized $^{129}$Xe gas." Thus, although each $^{129}$Xe term includes the word "gas," this word is used to name and descriptively track hyperpolarized noble gas produced via a hyperpolarizer to obtain a polarized "gas" product. Thus, as used herein, the term "gas" has been used in certain places to descriptively indicate a hyperpolarized noble gas product and may be used with modifiers such as solid, frozen, and liquid to describe the state or phase of that product at a particular point in time (such as at administration or during accumulation). U.S. Pat. No. 5,809,801 to Cates et al. describes a cryogenic accumulator for spin-polarized $^{129}$Xe. U.S. Pat. No. 6,079,213 to Driehuys et al., entitled "Methods of Collecting, Thawing, and Extending the Useful Life of Polarized Gases and Associated Accumulators and Heating Jackets", describes an improved accumulator and collection and thaw methods. The disclosures of these documents are hereby incorporated by reference as if recited in full herein.

As used herein, the terms "hyperpolarize," "polarize," and the like mean to artificially enhance the polarization of certain noble gas nuclei over the natural or equilibrium levels. Such an increase is desirable because it allows stronger imaging signals corresponding to better MRI and spectroscopy of the substance and a targeted area of the body. As is known by those of skill in the art, hyperpolarization can be induced by spin-exchange with an optically pumped alkali-metal vapor or alternatively $^3$He can be polarized by metastability exchange. See Albert et al., U.S. Pat. No. 5,545,396. Other methods may also be used, such as dynamic nuclear polarization ("DNP") and "brute force" methods which propose to cool the $^3$He or $^{129}$Xe to very low temperatures and then expose them to very high magnetic fields to enhance the thermal equilibrium polarization.

As discussed hereinabove, hyperpolarized $^{129}$Xe can be administered to a patient by inhalation or injection. If the administration modality is injection, $^{129}$Xe can be suspended in a carrier fluid or injected directly such as in gaseous form. However, regardless of what tissue is of interest, if the $^{129}$Xe is suspended in a carrier fluid, it is likely that the carrier fluid itself distorts the results of the spectra and/or substantially obscures a spectral peak of interest. The carrier fluid may also react with the target tissue (region of interest) and/or potentially produce compounds with molecules in or around the tissue of interest, which may thereby cause the chemical shift of hyperpolarized $^{129}$Xe to differ from that which would be observed with merely the tissue of interest and hyperpolarized $^{129}$Xe. Therefore, direct injection of gaseous $^{129}$Xe or administration via inhalation may be particularly suitable for certain embodiments or applications.

The present invention recognizes that hyperpolarized $^{129}$Xe is a sensitive probe for its environment. Specifically, spectroscopy utilizing hyperpolarized $^{129}$Xe is capable of detecting pathological conditions because of the frequency shift inherent in the response of $^{129}$Xe to its environment. The frequency shift observed with a tissue is characteristic of the tissue type and not significantly different between individuals. However, some variations between people based on race, gender and/or age are expected. These differences are due to the fact that some tissues typically vary in composition (e.g., bones become less dense with age). Typically a range of values characteristic of healthy tissues is expected. This range may be determined by large epidemiological studies. Alternatively, a "healthy" (substantially non-diseased or diseased to a lesser extent) standard may be acquired from an individual at an early stage (or at a different position or location in the body away from the diseased or abnormal target region). For the former, subsequent values acquired later in life or after certain treatments can be compared to this earlier standard. The term "pathological condition" refers to a biophysical structure or biochemical state or condition of a cell or cells, tissue, organ, or substance in the body. As used herein, the term includes healthy pathological conditions (i.e., the absence of overt pathology) as well as pathological conditions associated with diseases of the body which produce changes in structure or function and/or abnormal or progressive disorders.

Since different cell and tissue conditions can cause characteristic shifts, an exposure of hyperpolarized $^{129}$Xe to the human body may produce a characteristic pattern that demonstrates a superposition of the $^{129}$Xe frequency shifts apparent with each of the cell and tissue constituents. In healthy tissues, the location of spectral peaks (i.e. chemical shifts) and/or their sizes (as measured by spectral peak magnitudes and/or areas) may be different than when the cells comprising the tissues are altered by a pathological condition. For example, the fatty plaques indicative of late stage atherosclerosis or fatty unstable lesions of plaque may produce a respective "signature." As used herein, the term "signature" refers to a spectroscopic signal forming a characteristic pattern of a spectral peak or peaks at designated chemical shifts which may differ in size, shape, and/or location from that of a healthy or non-diseased state. With proper quantification of the signature, it may even be possible to distinguish between the early stages of a condition from later more developed pathology, even if the pathological tissue profile remains essentially the same throughout the disease progression but changes in cell proliferation or number, e.g., tumor size. Diagnostic in vivo tools such as these may enable early detection in disease progression, which may be successfully used in mass screening procedures, preferably even before potentially debilitating symptoms occur, and therefore allow for earlier intervention and consequentially potentially more effective treatment or even treatment which may prevent or delay the onset of symptoms and/or the disease itself.

Thus, by utilizing in vivo obtained signals of $^{129}$Xe spectrum "signatures," diseased states may be effectively identified, detected and/or diagnosed. Therefore, hyperpolarized $^{129}$Xe can be used in vivo as a non-invasive (or minimally invasive, if administered via injection) probe for pathological conditions. FIG. 1 is a schematic representation of a circulatory system. After hyperpolarized $^{129}$Xe is administered, e.g., via inhalation or injection as described hereinabove, the hyperpolarized $^{129}$Xe will travel throughout the body via the circulatory system until it is absorbed by a tissue or becomes completely depolarized.

Therefore, for example, when hyperpolarized $^{129}$Xe is delivered via inhalation, the $^{129}$Xe is absorbed by the blood in the alveolar capillaries. The Xe-blood mixture then is pumped via the pulmonary vein into the left atrium of the heart. The mixture then flows into the left ventricle and to the periphery and on into the region of interest (unless the region of interest is located within the pulmonary region) where MR spectroscopy can be accomplished. Obviously, if the pulmonary region is of interest, spectroscopic data can be acquired before the gas/blood mixture migrates to the heart.

This method may be used to detect pathological conditions such as, but not limited to, amyloid plaques associated with Alzheimer's disease, demyelination associated with multiple sclerosis, tumors, thrombi, and atherosclerotic plaques. In fact, any disease which has a characteristic hyperpolarized $^{129}$Xe signature due to a change in the biophysical or biochemical state of a cell or cells which comprise the region of interest may be advantageously detected with this method.

Figure 2:
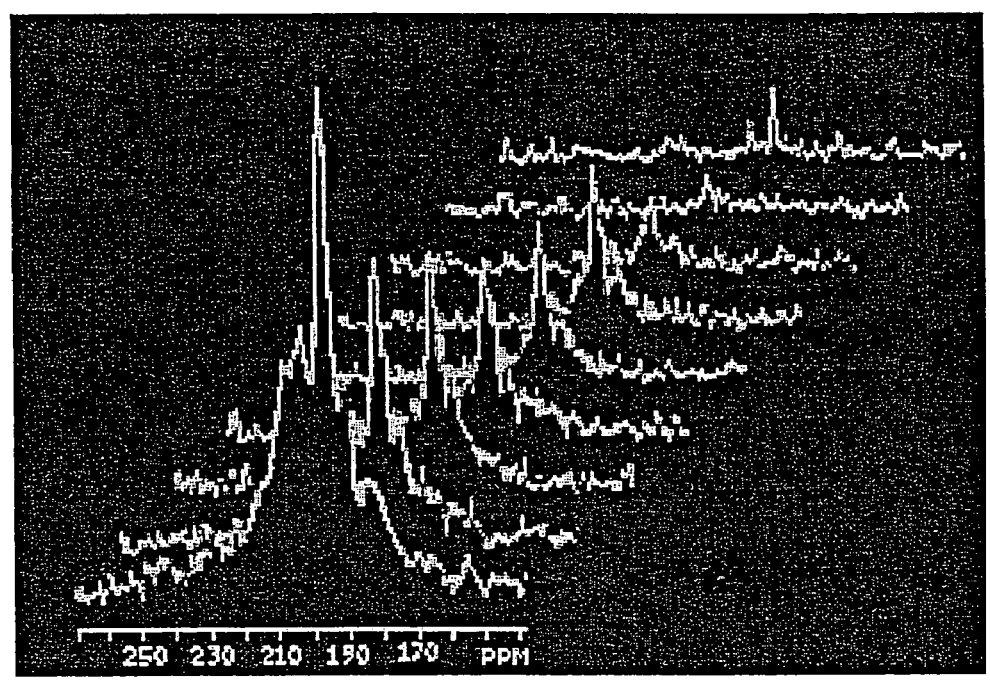
FIG. 2 is a screen printout of a set of brain spectra of a healthy human taken a few seconds after inhalation of 500 cc's of $^{129}$Xe polarized to about 2%.

One potentially important organ of interest for this type of analysis is the brain. One benefit of brain spectra is that the resulting spectra will not be substantially altered by factors such as blood flow, since brain perfusion is relatively constant despite environmental variables such as hormonal activity, sympathetic nerve activity and arterial blood pressure. FIG. 2 shows a set of brain spectra taken a few seconds after inhalation of 500 cc's of 2% polarized $^{129}$Xe. This healthy brain demonstrates a clear definable pattern of four distinct peaks representing the interaction of $^{129}$Xe with the different tissues/substances it is in contact with, such as blood cells, plasma, white matter, and grey matter.

As stated hereinabove, the observed spectra represent the environment in the brain and its interaction with $^{129}$Xe. As Table 1 shows, specific peaks can be assigned to specific environmental conditions, i.e., the presence of a particular cell and/or tissue type. Advantageously, therefore, noting the presence of a spectral peak not apparent in healthy tissues can be useful to detect certain pathological conditions characterized by unique cells and/or non-cellular substances such as tumors and plaques, where a characteristic change in tissue composition defines the pathological state.

In many cases, it would be of additional interest to quantify the progression of the diseased state, thereby giving an indication of the extent of damage to the tissue, for example, to differentiate a pea-sized tumor from a fist-sized tumor. However, some pathological conditions are identified as diseased predominantly by the excess or reduction of a signal associated with a healthy condition, which indicates that the observed chemical shifts may be similar in location in both "healthy" (substantially non-diseased) tissues compared to tissues with diseased conditions, but differ in peak magnitude, line shape (the line shape may be wider, lower, or present a differing spectral profile about the peak or peaks of interest), or area under the line associated with the peak. Therefore, in certain embodiments, differences in external factors that are not of interest, such as the initial polarization of the $^{129}$Xe, are taken into account to make accurate quantification possible. Because spectroscopy is quantitative in that the spectra have associated sizes (displayed by the profile of the line such as the height or magnitude of the peak and/or area under the spectral peaks), the ratio of the magnitudes of (or alternatively, the ratio of the areas within) one or more spectral peaks may be calculated and compared to evaluate or indicate a pathological condition. However, the parameter used to quantify events of interest must be chosen carefully. As known to those of skill in the art, the area contained within a spectral peak representing a chemical shift of interest may be a preferred parameter with which to quantify the chemical shift. This is because under some conditions (depending on exchange parameters), spectral peaks tend to be broad and short whereas under other conditions the spectral peaks are narrow and tall. Therefore, the magnitude of a spectral peak may not represent a condition accurately, whereas the area may be a more reliable parameter.

Regardless of what parameter is used to quantify spectral peaks, normalizing the spectral data may advantageously allow improved quantification of the condition of the patient. The term "normalizing" means to adjust the signal data of the spectral peak or peaks of interest to account for selected signal variables. This adjustment may include using the mathematic ratio of the values of certain peaks associated with selected known biomatter (RBC, plasma, etc) within the response spectrum to quantify the hyperpolarized gas signal in the region of interest. The adjustment may include using the polarization level (and/or quantity) of the administered gas to that used to obtain the reference spectrum to quantify the magnitude of the signal. As such, the normalization can use relative data and/or absolute data. For example, the ratio of the spectra for the blood to spectra of the brain tissue (the ratio of the magnitude or area of selected spectral peaks) can be calculated. Of course, other known chemical shift peak locations can also be used to normalize the value of the spectra peak of interest. The absolute data can include data associated with the polarization level of the gas as it is delivered to the patient and/or the amount of gas administered thereto (to account for signal strength).

For $^{129}$Xe NMR spectroscopy, spectral peaks at 213.0 ppm and 216.0 ppm (which usually cannot be easily resolved) represent oxygenated and de-oxygenated blood, respectively, according to Albert and Wilson (see Table 1). Additionally, brain tissue is typically measured around 197 ppm. During analysis, if the ratio of the signal for blood to brain tissue departs substantially from that which is considered "healthy" or "normal", for example, the spectra can indicate that a problem exists with perfusion (such as restricted blood vessels due to chronic hypertension). Alternatively, higher ratios of lipids in the cardiac or cerebral region (compared to dissolved phase $^{129}$Xe in the blood, for example) may indicate atherogenesis.

Figure 3:
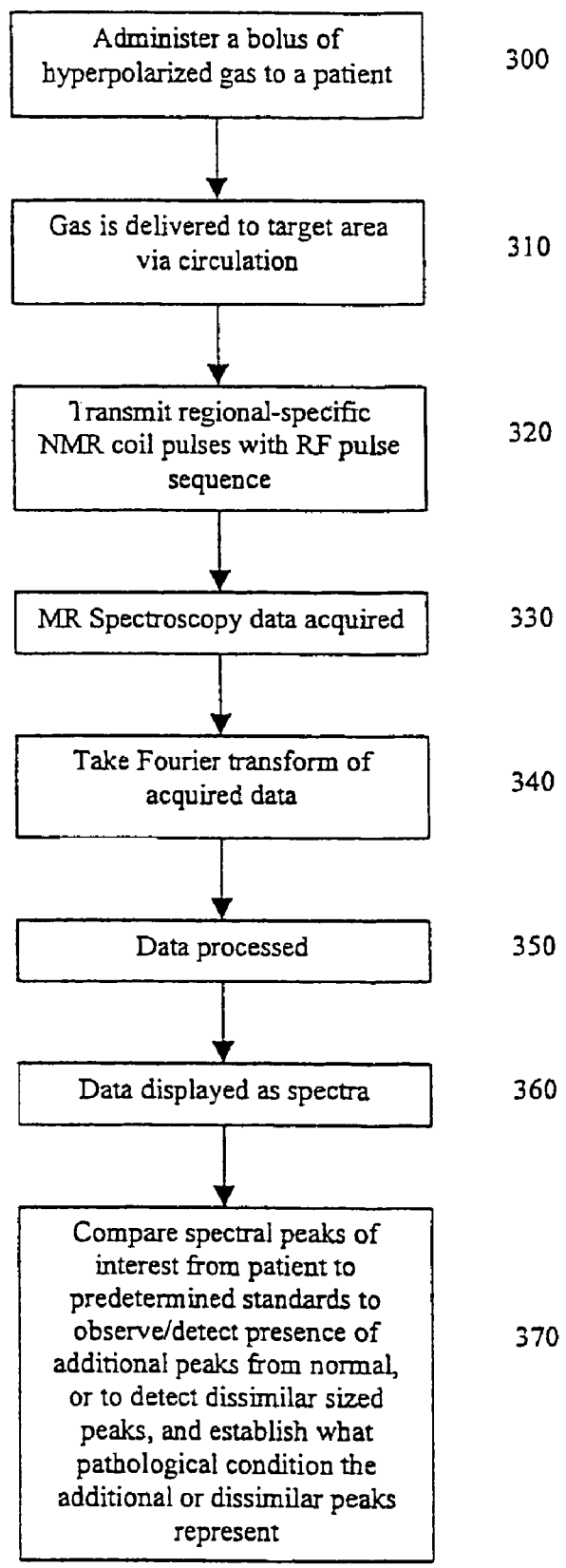
FIG. 3 is a flow chart depicting the chain of events followed to diagnose pathological conditions according to the present invention.

In practice, a diagnostic or screening procedure utilizing the instant invention can occur as shown in FIG. 3. A bolus of hyperpolarized $^{129}$Xe is administered to a patient in gas or liquid (or suspended in a liquid) form (Block 300) by injection or inhalation. The $^{129}$Xe is delivered to a target area (region of interest) via the circulatory system (Block 310). A region-specific NMR coil positioned over the region of interest transmits an RF pulse sequence (Block 320) and receives a FID (Block 330). As noted above, localizing gradients can also be applied about the region of interest so as to localize the resonance region. For example, localizing gradients can be applied so that a single one of the coronary arteries is excited (either the left or right). In any event, the Fourier Transform of the acquired data is then calculated (Block 340).

The transformed signal data can be further processed (Block 350) which may include, but is not limited to, one or more of subtracting background noise, filtering undesirable signal data (such as those portions of the signal or spectra attributed to carrier liquids or deposits in non-target tissue or blood and the like), determining the frequency shift and size of the shift for any number of peaks within pre-determined ranges in the spectrum, and normalizing the data such as finding the ratios between magnitudes and/or areas of different spectral peaks within the response spectrum or accounting for polarization level and amount of polarized gas delivered to the subject. The processed data can be visually displayed (Block 360). In any event, a clinician or physician, computer, or program code can compare the signal data from the patient to that of a reference standard (Block 370) to diagnose and/or detect a pathological condition or absence thereof. The comparison can analyze whether there are additional peaks or missing peaks from a norm or whether there are dissimilar sized peaks and establish the correlation to what pathological condition may be indicated. The reference standard can be spectra generated from corresponding hyperpolarized gas NMR spectroscopic response signals of one or more "healthy" subjects or based on a historical (signal obtained in the past) response signal (s) of the patient undergoing analysis.

Typical spectra standards for target tissues, regions, or pathologic conditions may vary depending on certain parameters in population segments such as age, gender, and/or race. For example, the composition of some tissues differs with age and gender. Most likely, a statistically valid range of "healthy" or undiseased characteristics established by an epidemiological study can be determined and used as a reference standard, and deviants outside this range or on the outer edges of this range can be monitored closely for and/or notified of an observed or potential pathological condition. Alternatively, as mentioned hereinabove, an early set of spectra can be acquired for an individual and spectra acquired later in life (or after and treatments) can be compared to the earlier values to provide an internal individual-specific standard. Advantageously, an individual-specific standard additionally enables monitoring disease progression and treatment efficacy.

Atherosclerosis in coronary arteries is one condition for which in vivo $^{129}$Xe spectroscopy has a great potential to make a significant impact in early detection of pathology. Atherosclerosis is a multi-stage progressive disease, in which only the late stages are characterized by noticeable circulatory compromise, calcified lesions, and thrombosis. Often, if the disease is only detected at these later stages, the condition's progression cannot be reversed or even retarded, which may result in a significant reduction in the patient's quality of life. Early stages of atherosclerosis are characterized by fatty streaks which comprise lipid-filled foam cells in the intima and very little extracellular lipid. Generally the foam cells are of macrophage derivation, although some are from smooth muscle cells. As the disease progresses, lipid, collagen, and proteoglycans accumulate in the extracellular matrix and fibrous plaques form. Macrophages accumulate in the arterial wall and are captured there, oxidizing and accumulating oxidized low density lipoprotein (LDL). Later stages of the disease involve smooth muscle cell and collagen accumulation of LDL as well, and fully developed lesions eventually develop and protrude into the lumen, thereby reducing blood flow to downstream tissues. Blood flow can be completely blocked, causing platelets to adhere and risking embolism and thrombosis. Complications from atherosclerosis are believed to be the leading cause of death in the United States and Europe. Early detection of this disease, long before fully developed lesions form, would be extremely beneficial for improved treatment regimens.

One critical location where atherosclerosis is common is in the coronary arteries. One obvious difficulty in trying to investigate this area with hyperpolarized $^{129}$Xe is that the $^{129}$Xe in the blood (both associated with blood cells and in dissolved phase in the plasma) within the heart chambers creates a much stronger signal than the $^{129}$Xe of interest within the much smaller coronary vessels.

Figure 4:
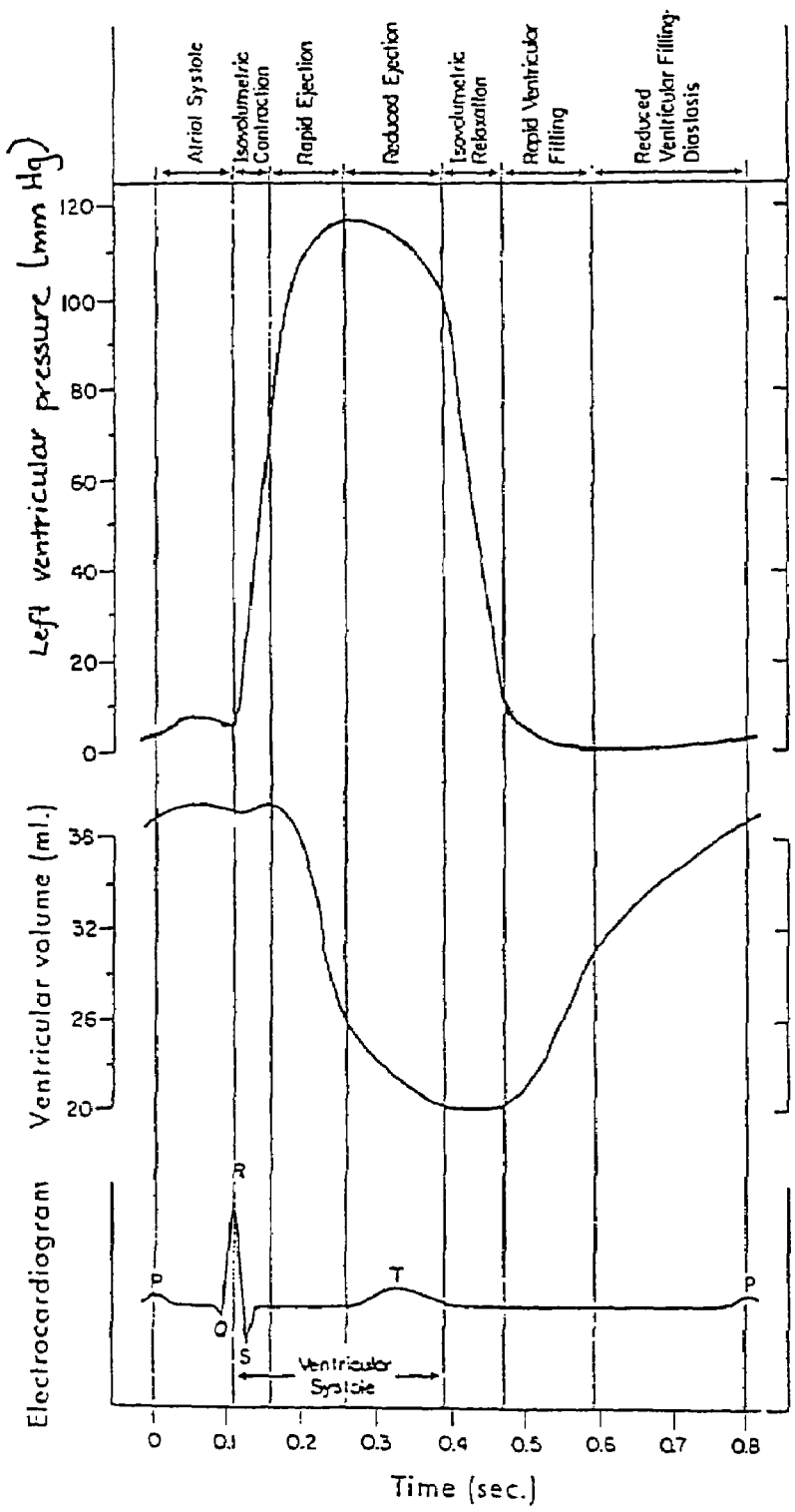
FIG. 4 is graph of left ventricular pressure correlated in time with ventricular volume and an electrocardiogram for a complete cardiac cycle.

One technique for addressing this difficulty includes taking a background spectrum which represents a heart "full" of polarized $^{129}$Xe and blood (yet none in the coronary arteries) and subtracting this background from all subsequent spectra. As shown in FIG. 4, one way to achieve this subtraction technique is through cardiac gating. Since very little blood goes directly from the heart chambers into the myocardium, the majority of the blood nourishing the myocardium exits the left ventricle through the aorta and into the coronary arteries. Therefore, it is only after left ventricular contraction (i.e., systole) that the $^{129}$Xe enters the coronary arteries and myocardium. Thus, in a preferred embodiment, the background spectrum is acquired before ventricular systole, so that the background scan can be used to represent a "full" heart with polarized $^{129}$Xe and blood to enhance the signal in the coronary vessels. For further discussion of exemplary background and cardiac gating methods, see co-pending U.S. application Ser. No. 09/271,476, the contents of which are hereby incorporated by reference as if recited in full herein.

As shown in FIG. 4, the ventricle is full and fairly constant in volume during atrial systole and isovolumetric contraction (see the middle graph). Therefore, the background scan can be acquired anytime during this interval.

Advantageously, subsequent spectra can be obtained at substantially the same point in the cardiac cycle to reduce potential effects due to different blood volumes in the heart between background and subsequent scans. Therefore, subsequent scans are preferably acquired at substantially the same point in the cardiac cycle (i.e., gated in the same manner) as the background scan. However, if the $T_1$ of the $^{129}$Xe in the blood and vessels of interest is not sufficiently long to permit waiting almost an entire cardiac cycle after ventricular systole to acquire a spectrum, it is also possible to take the background spectrum at a different point in the cardiac cycle from the subsequent spectra. Alternatively, both the background spectrum and subsequent spectra can be acquired immediately after ventricular systole, triggered by the "T" wave of the electrocardiogram (see bottom graph of FIG. 4). Although the volume of the ventricle is increasing during this period as shown in the middle graph of FIG. 4, the aortic blood flow is low because the aortic valve has closed. However, scanning immediately after systole may be less preferable in obtaining a good background scan.

As known to those of skill in the art, pulsing to produce a large flip angle (between about 45-90 degrees, and typically about 90 degrees) excitation pulse results in a better SNR (signal to noise ratio) but destroys more polarization over small flip angle pulses. Therefore, at least the initial spectra (i.e. before the background spectrum) should be pulsed such that small flip angles (approximately 30° or less) are produced. If a better SNR is desired for later spectra, larger flip angles can be induced in subsequent spectra once a predetermined threshold level of hyperpolarized Xe has been attained. Small flip angles are particularly advantageous when examining the heart because the heart at any time contains the blood supply soon to be distributed throughout the body. Therefore, obviously a large flip angle will deleteriously affect the $^{129}$Xe polarization in the heart and thereby make it difficult to obtain spectra immediately thereafter. However, if a single spectrum (or alternatively spectra obtained in substantially large time intervals such that the hyperpolarized $^{129}$Xe supply is replenished) is desired, it may be advantageous to use large flip angles to obtain the benefits of a better SNR. Co-pending U.S. patent application Ser. No. 09/271,476 describes the use of large flip angle pulses and pulse sequences using hyperpolarized noble gas, the contents of which are hereby incorporated by reference as if recited in full herein.

Figure 5:
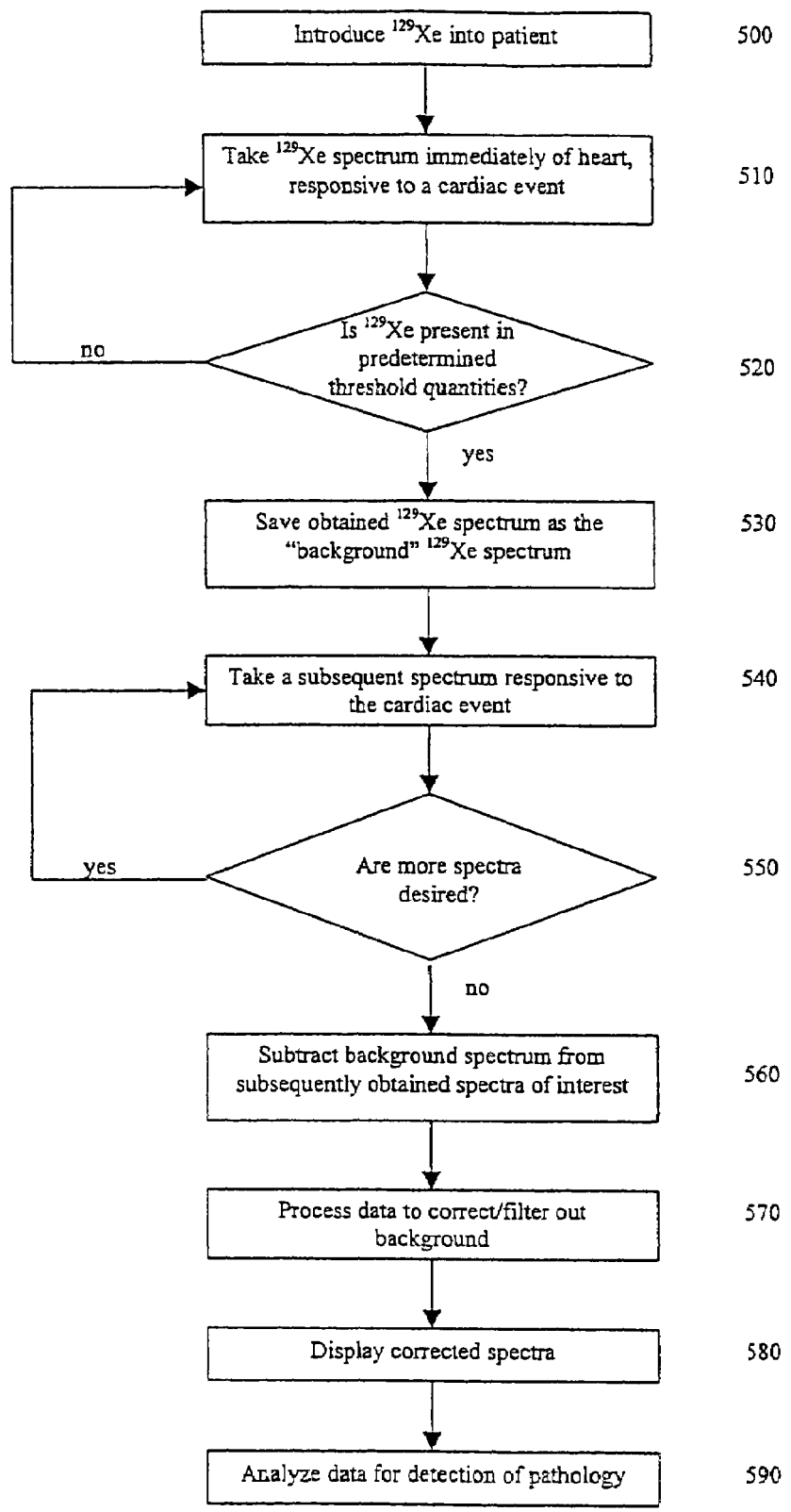
FIG. 5 is a flow chart depicting a procedure for detecting $^{129}$Xe spectra from the coronary arteries according to the present invention.

The block diagram of FIG. 5 outlines one method of compensating for the hyperpolarized $^{129}$Xe signal in the heart to enhance the hyperpolarized gas signal in the region of interest. First, a bolus of hyperpolarized $^{129}$Xe is introduced into a patient via inhalation or injection (Block 500). Subsequent thereto (and preferably immediately afterwards), a MR spectroscopy signal or spectrum of the heart is obtained, the excitation signal preferably being triggered and transmitted responsive to a predetermined cardiac event (Block 510). If a predetermined threshold amount of $^{129}$Xe is not present, as determined by observing the size of the peak representing plasma-dissolved phase $^{129}$Xe, for example (i.e., a spectral peak with a chemical shift (compared to gas phase $^{129}$Xe) at around 195.6 ppm), additional spectra of the heart are acquired until the threshold has been reached. If the threshold of $^{129}$Xe has been achieved (indicating that hyperpolarized $^{129}$Xe has reached the heart in sufficient quantities), the spectrum data is saved as the "background spectrum" for future spectra (Block 530). Once the threshold has been reached and a suitable background spectrum has been obtained (Block 530), the heart can be intermittently interrogated (Blocks 540 and 550), preferably initiated by the same cardiac event which was used to gate the background scan. In certain embodiments, once all desired spectra have been acquired, the background spectrum can be subtracted from all subsequent spectra (Block 560) to provide corrected data.

Figure 11A:
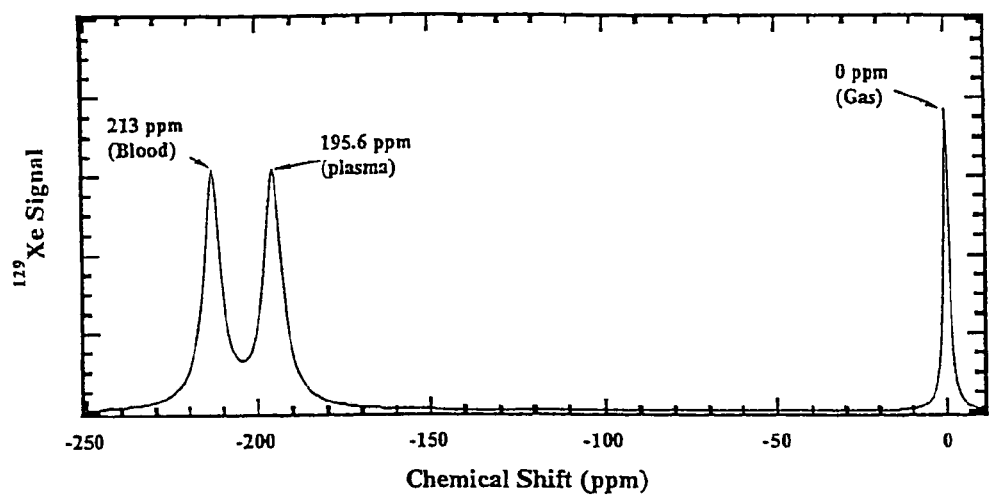
FIG. 11A is a simulated background spectrum of an individual where the heart chambers contain substantial amounts of hyperpolarized $^{129}$Xe gas/blood mixture but the coronary arteries are substantially free of hyperpolarized $^{129}$Xe.
Figure 11B:
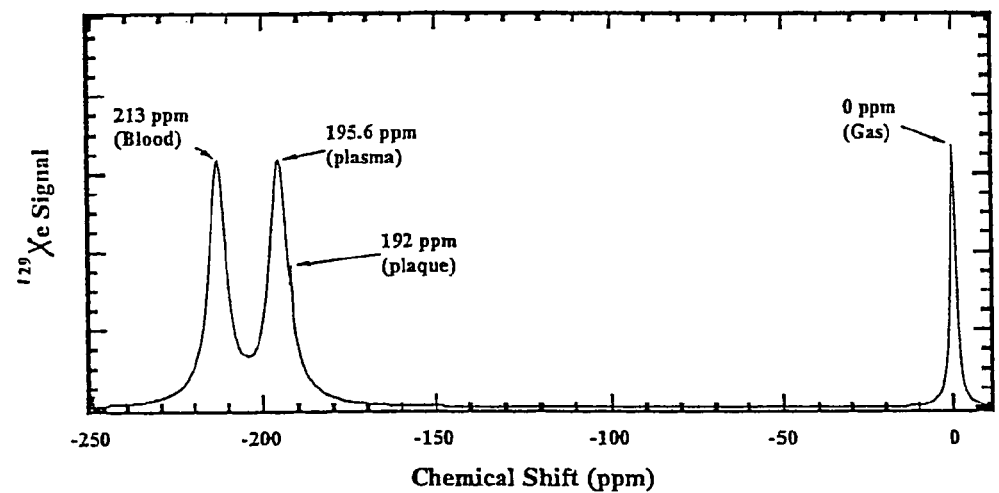
FIG. 11B is a simulated spectrum of an individual's heart after hyperpolarized $^{129}$Xe is in both the heart chambers and the coronary arteries.

A simulated sample background spectrum is illustrated in FIG. 11A. As shown in FIG. 11A, the chemical shifts representing $^{129}$Xe in the blood and plasma are prominent. A simulated spectrum illustrating a post-background spectrum is shown in FIG. 11B. As shown, very little (if any) difference between the two spectra (i.e. the spectra of FIG. 11A and FIG. 11B) can be observed because of the large spectral peaks associated with $^{129}$Xe in the blood in FIG. 11A.

Figure 11C:
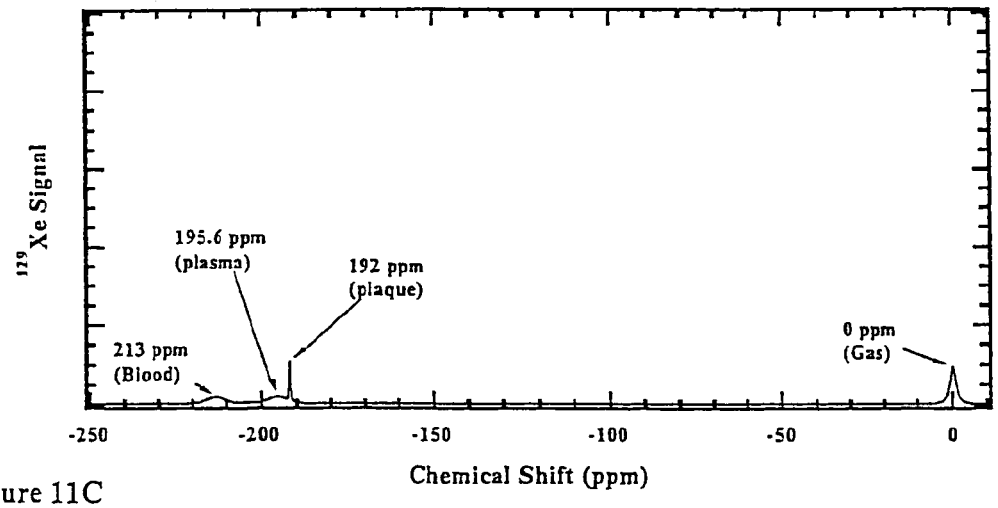
FIG. 11C is a simulated corrected spectrum of the spectrum shown in FIG. 11B minus the background spectrum of FIG. 11A.

As shown in the simulated image in FIG. 11C, the subtracted corrected spectrum has a substantially smaller signal associated with the free gas phase (at 0 ppm), the plasma-dissolved phase $^{129}$Xe (at about 195.6 ppm) and the dissolved phase $^{129}$Xe in the red blood cells (at approximately 213 ppm). Advantageously, a spectral peak at about 192 ppm representing $^{129}$Xe dissolved in atherosclerotic plaques is substantially more prominent after background subtraction.

After background subtraction, the corrected data is processed, including, but not limited to, identifying and measuring spectral peaks of interest. Finally, the corrected spectra can be displayed (Block 580, FIG. 5) and further analyzed for the detection of pathology in vivo (Block 590, FIG. 5) such as, but not limited to, area calculation and/or ratio calculation of the associated peak(s) as described herein.

Additional information can also be gathered from hyperpolarized $^{129}$Xe spectra using alternative data (besides chemical shift) and pulse sequences. For example, diseased tissues may have different diffusion coefficients, or display unique contrast parameters such as $T_2^*$, $T_2$, $T_1$, and/or Tip. Spectroscopy methods to observe changes in these parameters are well known to those of skill in the art. Spectroscopy skillfully utilizing these parameters (e.g., by adeptly designing pulse sequences) and others (such as flow techniques) may facilitate targeting biological phenomenon of interest and/or assist background filtering.

For example, as estimated by Wolber et al, $^{129}$Xe exchanges rapidly between red blood cells and plasma (on the order of about 2 to 3 ms). However, when $^{129}$Xe is in an environment where it does not exchange rapidly, $T_2$ was estimated by the same group to be approximately 320 ms. Because of its lipophilic, nature, hyperpolarized $^{129}$Xe is unlikely to leave arterial plaques readily, causing the $T_2$ of $^{129}$Xe to be relatively long in arterial plaques. In other words, the $T_2$ associated with red blood cells and plasma would be short, while that associated with plaques would be relatively long. Advantageously, therefore, even if the chemical shift characteristic of atherosclerotic plaques is the same or very similar to that of red blood cells or plasma (i.e., observed near the same frequency), the spectral peak of interest could be advantageously examined by utilizing a $T_2$-weighted sequence.

Figure 9A:
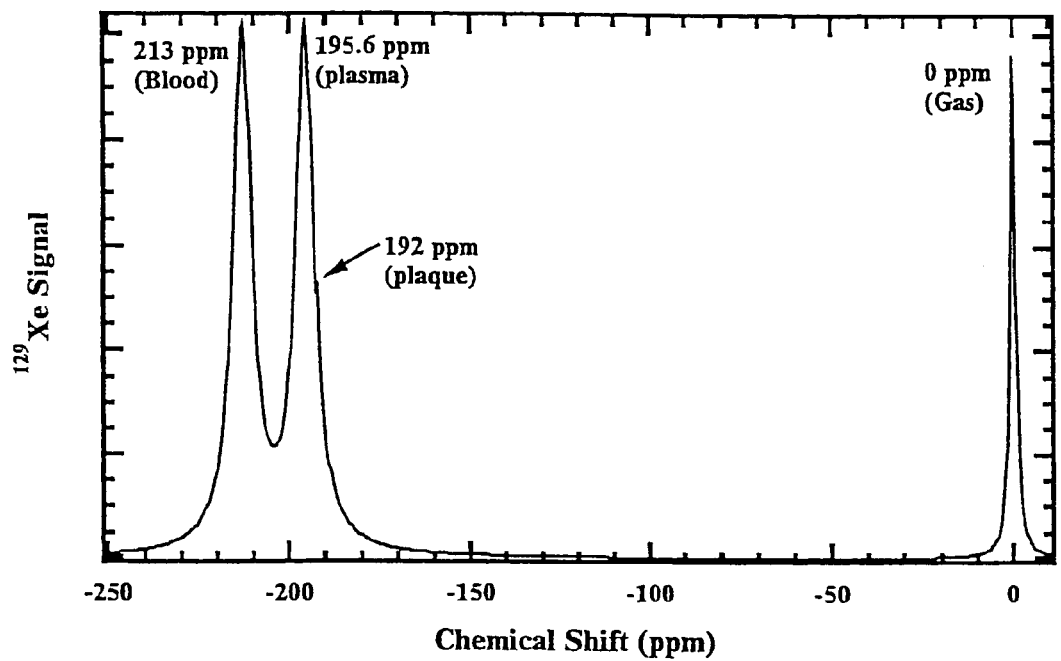
FIG. 9A is a simulated spectrum denoting spectral peaks due to blood, plasma, fatty plaques, and free $^{129}$Xe gas.

FIG. 9A depicts a simulated spectrum, assuming operation at 1.5 T and assuming that the magnitudes of the $^{129}$Xe in red blood cells and plasma are ten times as large as that observed in atherosclerotic plaques (primarily due to the relatively large amount of blood in the heart). The spread in frequency observed in the Fourier Transformed spectrum of a given peak can be calculated by $$\Delta v \approx \frac{1}{2\pi T_2}$$

Therefore, assuming 1.5 T (therefore a $^{129}$Xe resonance frequency of about 17.7 MHz):

TABLE 2

Frequency shifts in ppm for a simulated atherosclerotic plaque and blood.

| Component | Chemical Shift | Amplitude (relative) | $T_2$ (ms) | $\Delta v$ (Hz) | $\Delta v$ (ppm) |
| --- | --- | --- | --- | --- | --- |
| $^{129}$Xe - gas | 0 ppm | 10 | 10 | 16 | 0.9 |
| $^{129}$Xe - plasma | 195.6 ppm | 10 | 3 | 53 | 3 |
| $^{129}$Xe - RBC | 213 ppm | 10 | 3 | 53 | 3 |
| $^{129}$Xe - plaque | 192 ppm | 1 | 100 | 1.6 | 0.09 |

As FIG. 9A shows, the $^{129}$Xe chemical shift in the plaque is typically substantially obscured by the signal from the plasma and the blood. Although a small peak is typically visible, it cannot be readily distinguished from the nearby spectral peak representing $^{129}$Xe in plasma. If this were a real spectrum and not a simulated spectrum, the inherent noise could act to substantially obscure the small shoulder associated with the plaque that is barely discernible in FIG. 9A.

Figure 9B:
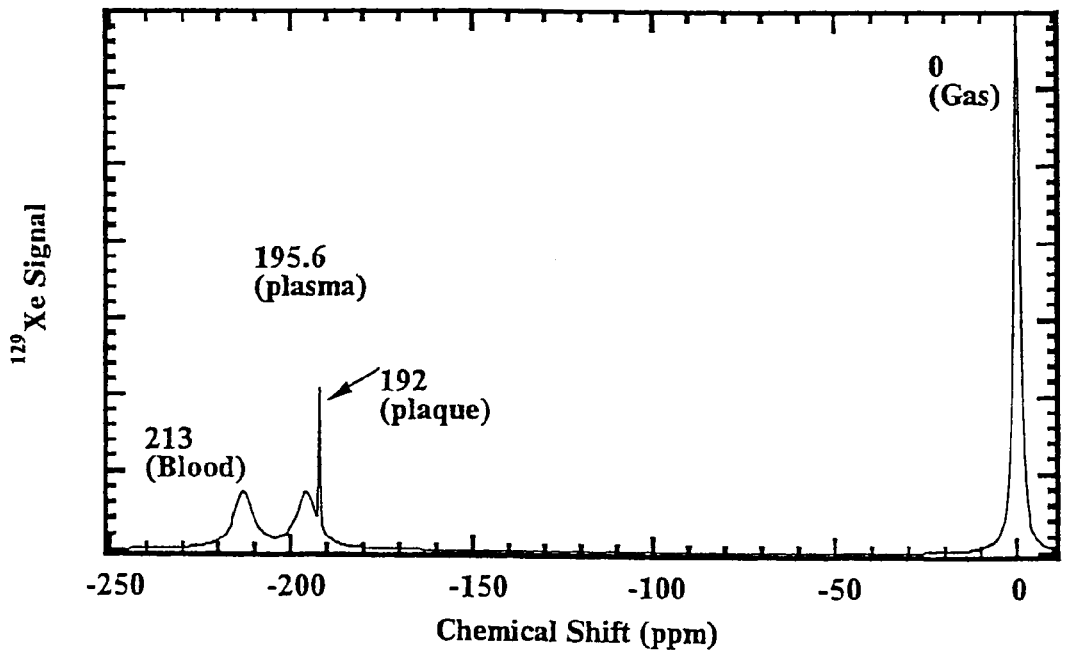
FIG. 9B is a simulated spectrum under the same conditions as FIG. 9A, but acquired with a $T_2$-weighted pulse sequence according to the present invention.

However, as shown in FIG. 9B, with a different pulse sequence, a completely different spectrum is observed. The simulated spectrum of FIG. 9B assumes that a $T_2$-weighted pulse sequence is used with a delay of about 10 ms. With the 10 ms delay, the plasma and blood resonances are suppressed by a factor of about 28, whereas the plaque resonance of interest is only suppressed by a factor of about 1.1. Therefore, by taking advantage of inherent tissue or metabolic properties, identifying the $^{129}$Xe signal associated with a phenomenon or target tissue of interest can become more readily discernible. Of course, the signal of interest need not be actually displaced at all, because a computer or program means can perform the necessary computations/algorithms to then identify the value of the targeted tissue/region/ condition.

In other embodiments, the methods of the present invention can use the $T_1$ contrast parameter to obtain relevant data regarding the pathological condition. That is, the $T_1$ of the polarized gas may be enhanced over the $T_1$ in blood as it is taken up into lipid rich or other polarization life extending or enhancing environments. Thus, the transmittal of the excitation RF pulse and associated signal acquisition can be performed such that it is delayed and obtained a period after administration of the polarized gas to the subject. This delay can be timed such that it is sufficient for the hyperpolarized gas in the blood to decay to a low, negligible or dissipated level while the polarized gas taken up into the tissue or cells in the region of interest still has a sufficiently viable life to allow the spectrum to be obtained with signal data of the hyperpolarized gas only for that in the region of interest. For example, delaying the signal acquisition to about 10 seconds to 1 minute (typically about 20 seconds to 30 seconds) after administration of the hyperpolarized gas to the subject will allow the hyperpolarized gas in the blood to decay. In certain embodiments, the hyperpolarized gas will naturally decay in blood in about 5-6.4 seconds, while the hyperpolarized gas taken up in certain bio-environments (such as fatty tissue) may be viable or retain a sufficient polarization level to allow for spectroscopic detection for between about 10-60 seconds longer.

In certain embodiments, the polarized gas can be delivered via breath-hold delivery as conventionally delivered for imaging applications. In this type of delivery, a patient inhales a quantity of hyperpolarized gas, holds his or her breath a suitable time, and then exhales and resumes normal breathing. To take advantage of the natural $T_1$ decay in the body and the longer $T_1$ of the hyperpolarized gas in certain bio-environments, using the $T_1$ as a contrast parameter to enhance the signal over non-targeted signal hyperpolarized gas signal information, the signal acquisition can commence while the patient exhales or after the patient resumes normal breathing. Preferably, the signal acquisition is carried out at about 10 seconds to about 1 minute, and preferably at about 20-30 seconds, after the patient exhales the breath-hold lung volume.

Alternatively, as known by those of skill in the art, the status of the walls of the carotid arteries can be monitored as an indicator of the coronary arteries in lieu of investigating the coronary arteries directly. This is due to the fact that the carotid arteries often develop plaques which can indicate plaque development in the coronary arteries. Advantageously, using the carotid arteries instead of the coronary arteries to monitor atherosclerosis obviously substantially reduces the background signal problem discussed hereinabove. Furthermore, a small sensitive coil can be placed directly on the neck over one or more of the carotid arteries to better transmit and detect signals to and from the carotid arteries and blood therein. Therefore, as is true for any part of the body which is not near the heart and which can be interrogated by transmitting an RF pulse through a local coil, pulses which produce large flip angles will not deleteriously affect future spectra, since the signal source (hyperpolarized $^{129}$Xe in the blood) is continually replenished and unaffected by the RF pulse transmitted by the local coil. Therefore, large flip angles (more than about 30°) can thereby advantageously be utilized in these situations to obtain the benefits of a better SNR.

The last step of used to detect pathology generally involves analysis of the data. The analysis evaluates one or more selected parameters associated with the peak spectra. This can include, but is not limited to, the peak amplitude or magnitude of the spectra of interest, the associated line shape or line width, the area under the curve of the spectra peak or peaks of interest, and the like. In certain embodiments, the data is corrected to account for in vivo background data (e.g., the background data is subtracted of filtered).

Figure 10A:
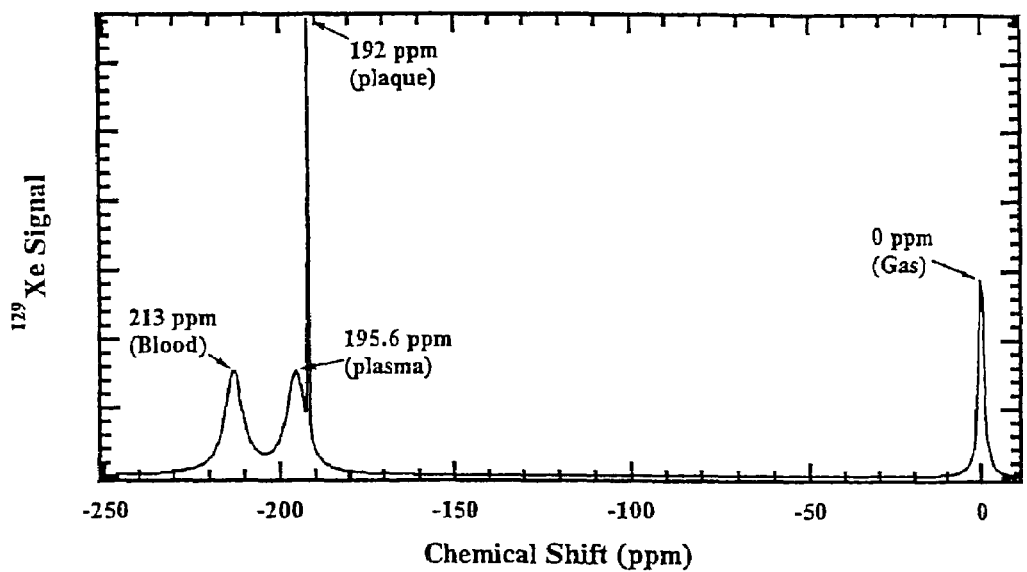
FIG. 10A is a simulated spectrum of the coronary arteries of a person who has significant fatty plaques indicative of atherosclerosis.
Figure 10B:
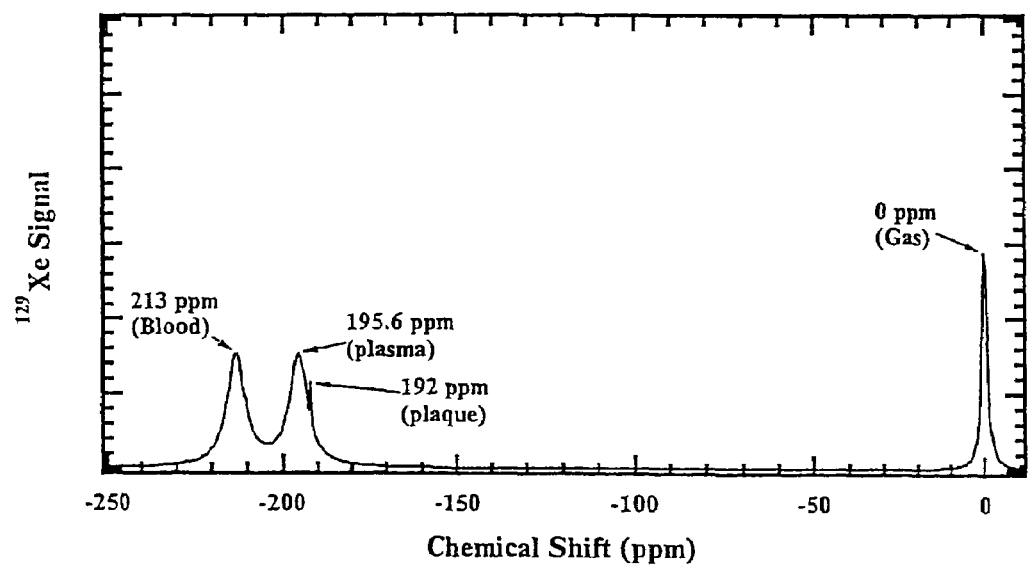
FIG. 10B is a simulated spectrum of an individual who does not have significant detectable coronary artery plaques. This spectrum is therefore representative of a "reference" or "standard" spectrum.

The analysis, such as for the embodiment described in FIG. 5, can include comparing a background-corrected spectrum (or spectral peaks of interest within a corrected spectrum) to a predetermined reference standard. FIGS. 10A and 10B illustrate one way to compare two spectra to obtain an indication of the extent of a diseased state. FIG. 10A depicts a simulated spectrum of a severely atherosclerotic region where plaque development is extensive. Preferably, as mentioned hereinabove, a background spectrum has already been subtracted if this spectrum is of the coronary arteries to eliminate the much larger signal from the blood in the heart chambers. As mentioned hereinabove, often (as is done in FIG. 10A) a specific cell or tissue type can be associated with a specific chemical shift (compared to gas phase hyperpolarized $^{129}$Xe) in the spectrum. For example, FIG. 10A associates the peak located at 192 ppm with an atherosclerotic plaque. Therefore, comparing the peak located at 192 ppm in FIG. 10A with that at the same chemical shift in FIG. 10B (the latter of which is a simulated spectrum of a "healthy" or substantially undiseased arterial condition also after subtracting the signal associated with the blood in the heart chambers and therefore representative of a "healthy reference" spectrum), clearly indicates a difference between the two conditions. Furthermore, by normalizing the peak (using one or more of the line shape or peak magnitude, area under the peak, or peak width) located at 192 ppm with (for example) the peak at 0 ppm (gas phase $^{129}$Xe), a physician, computer, or program product can compare the observed normalized peak sizes with that of a healthy standard as discussed hereinbelow. Further the presence or absence of a peak from the standard to the response signal under analysis or the difference in magnitude of the peak (area under the curve of the spectra peak or associated line shape or the amplitude of the peak) or other quantifiable parameter of the spectral peak or peaks of interest can be used to diagnose or determine the likelihood of a pathological condition under analysis. It is noted that the use of the peak at 192 ppm was selected for discussion purposes because this is a location associated with fat or fatty tissue. In operation, other chemical shift locations may be identified or used as appropriate to the pathological condition or conditions under analysis.

As mentioned hereinabove, brain spectroscopy is feasible even with inhaled $^{129}$Xe because $^{129}$Xe easily traverses the blood-brain barrier and blood flows to the brain in quantities sufficient for spectroscopy. FIG. 2 shows spectra taken from a healthy human brain in vivo. Atherosclerosis, as discussed hereinabove, is also of interest in the brain tissue, because it can lead to strokes. Advantageously, background problems such as those encountered in imaging coronary arteries is significantly diminished in brain spectroscopy.

Other conditions, such as Alzheimer's disease, could also benefit from hyperpolarized $^{129}$Xe spectroscopy of the brain. Alzheimer's disease is one of the most common causes of dementia, or loss of mental function. The disease progresses from a loss of memory to complete incapacity to perform simple tasks and care for oneself. Many people afflicted with Alzheimer's disease live for many years and eventually die from pneumonia or other diseases. Although the average lifespan of an Alzheimer patient after diagnosis is about 4 to 8 years, some patients live for more than 20 years with the disease. Although estimates of the number of people afflicted with the disease range from 25 to 50 percent of the population who is 85 or older, it is clear that the percentage of people afflicted with the disease doubles with every decade of life. As the average life expectancy increases, therefore, degenerative diseases such as Alzheimer's disease will become more prevalent.

Despite large amounts of research, Alzheimer's disease is still only partially understood. The disease begins in the entorhinal cortex and proceeds to the hippocampus and cerebral cortex and to other regions of the brain. The affected regions characteristically contain degenerated and dead neurons. A true diagnosis still can only occur in an autopsy where the characteristic neuritic plaques outside and around the neurons, as well as neurofibrillary tangles inside the nerve cells, are observed. To date, there is no reliable, valid, early diagnostic marker for Alzheimer's disease. Early diagnosis of Alzheimer's disease is important because many other diseases, such as tumors, strokes, severe depression, and thyroid problems, whose symptoms mimic those of Alzheimer's disease, have cures or at least effective treatments when administered early. Additionally, the only drug on the market to treat Alzheimer's disease is significantly more effective if administered during the early stages of the disease. Alzheimer's disease is therefore well suited to be detected with $^{129}$Xe spectroscopy because the disease involves characteristic and unique changes in the tissues. $^{129}$Xe spectroscopy may detect structural changes in tissue type and display a chemical shift signature, which may advantageously enable a physician to diagnose Alzheimer's disease definitively in vivo before death, and preferably early in the progression or near the onset of the disease.

Quantifying the spectral peaks representing chemical shifts can be of critical importance in determining the extent of the disease for progressive diseases such as atherosclerosis and neurological diseases (such as Parkinson's disease, multiple sclerosis, and Alzheimer's disease), because the stage of the disease may determine the desired course and type of treatment. Therefore, for accurate quantification of hyperpolarized $^{129}$Xe as an indicator of disease, secondary conditions such as the polarization of the administered gas and the volume of hyperpolarized gas administered to the subject are preferably accounted for in any $^{129}$Xe spectroscopic analysis. One quantification method according to the present invention is to take the ratio of two observed spectral peaks of interest such as described hereinabove. For example, in atherosclerosis, the intimal layer decreases while the amount of lipid contained in the vessel walls increases. Therefore, a ratio of the peaks representing the destruction of the intimal layer and the accumulation of lipids in the media may be of clinical importance. Advantageously, this method inherently additionally factors out differences between people in alveolar capillary uptake of $^{129}$Xe if administered by inhalation.

Alternatively, even if a single "signature" peak at a specific chemical shift is reliably indicative of a diseased state (such as plaques in the brain characteristic of Alzheimer's disease), a physician would typically still be interested in knowing the extent of the diseased tissue. Therefore, the present invention provides methods to quantify the identified signature or characteristic peak(s).

In certain embodiments, to account for secondary factors, the present invention normalizes the peak of interest by taking the ratio of the size of the observed peak to a second peak which is always present but not necessarily of any interest (such as the dissolved phase $^{129}$Xe peak (such as that representing $^{129}$Xe in the plasma) or even the gas phase $^{129}$Xe). Therefore, a normalized value for a single spectral peak of interest can be obtained. Normalizing a spectral peak representing a chemical shift of interest by analyzing/comparing the dissolved phase $^{129}$Xe (in the plasma or RBCs) advantageously also inhibits other factors (such as other transport deficits or metabolic disorders) from undesirably influencing or affecting the results. Since the dissolved phase signal in the blood (e.g. plasma) is effectively the "supply" of hyperpolarized $^{129}$Xe that the tissue sees, it may be appropriate to determine the volume of hyperpolarized $^{129}$Xe in a tissue with respect to its supply as described hereinabove.

Figure 8:
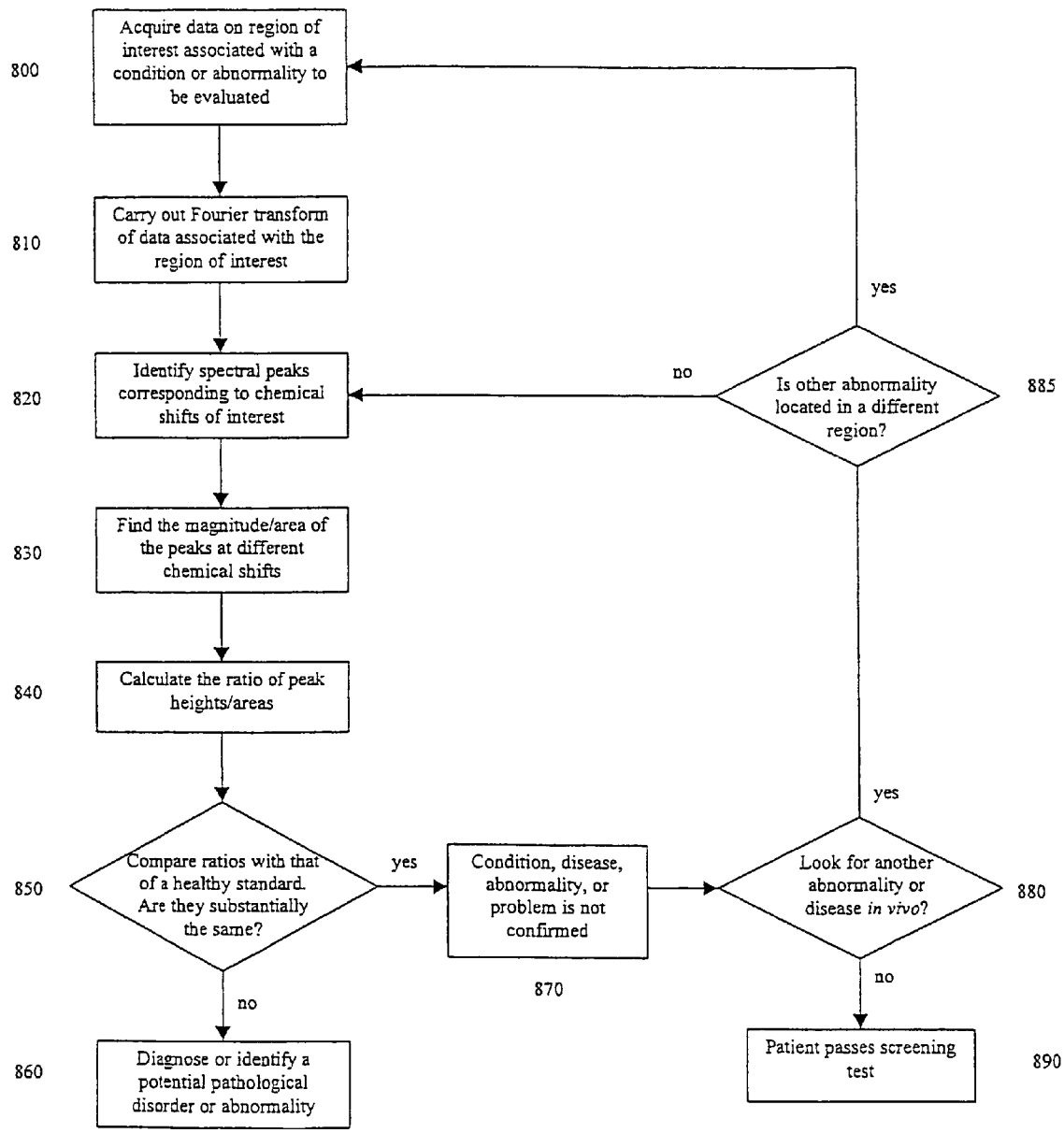
FIG. 8 is a flow chart depicting an alternative method for normalizing spectra according to the present invention.

Turning to FIG. 8, a normalization procedure according to the present invention can be performed after any number of spectra have been acquired, although preferably background subtraction (if desired) is performed prior to normalization. Data is acquired (preferably through NMR spectroscopy as described hereinabove) of a patient's region of interest (Block 800). The Fourier transform of the resulting data is determined (Block 810), and spectral peaks at frequencies of interest are identified (Block 820). The size of a first and a second spectral peak of interest is calculated either by magnitude or area as described hereinabove (Block 830), and the ratio of the magnitudes and/or areas of two peaks is determined (Block 840). If there is only one peak of interest, its size can be normalized by an internal standard, such as the size of the plasma-dissolved phase $^{129}$Xe spectral peak, as described hereinabove. The calculated ratio is then compared to that obtained in a healthy person, across a population segment, or to an earlier data set from the same patient (Block 850). If the two ratios are not substantially the same, a pathological disorder can be diagnosed, identified as being likely, or deemed to have progressed or regressed (Block 860). However, if the two ratios are substantially the same, the suspected problem is not confirmed or a change in disease status has not occurred (Block 870) and either further evaluation for other disorders (by looking at different spectral peaks or interrogating another region of interest) can be accomplished or the patient can be declared healthy or stable (Block 890) and/or a "baseline" can be stored for future comparison.

Figure 7:
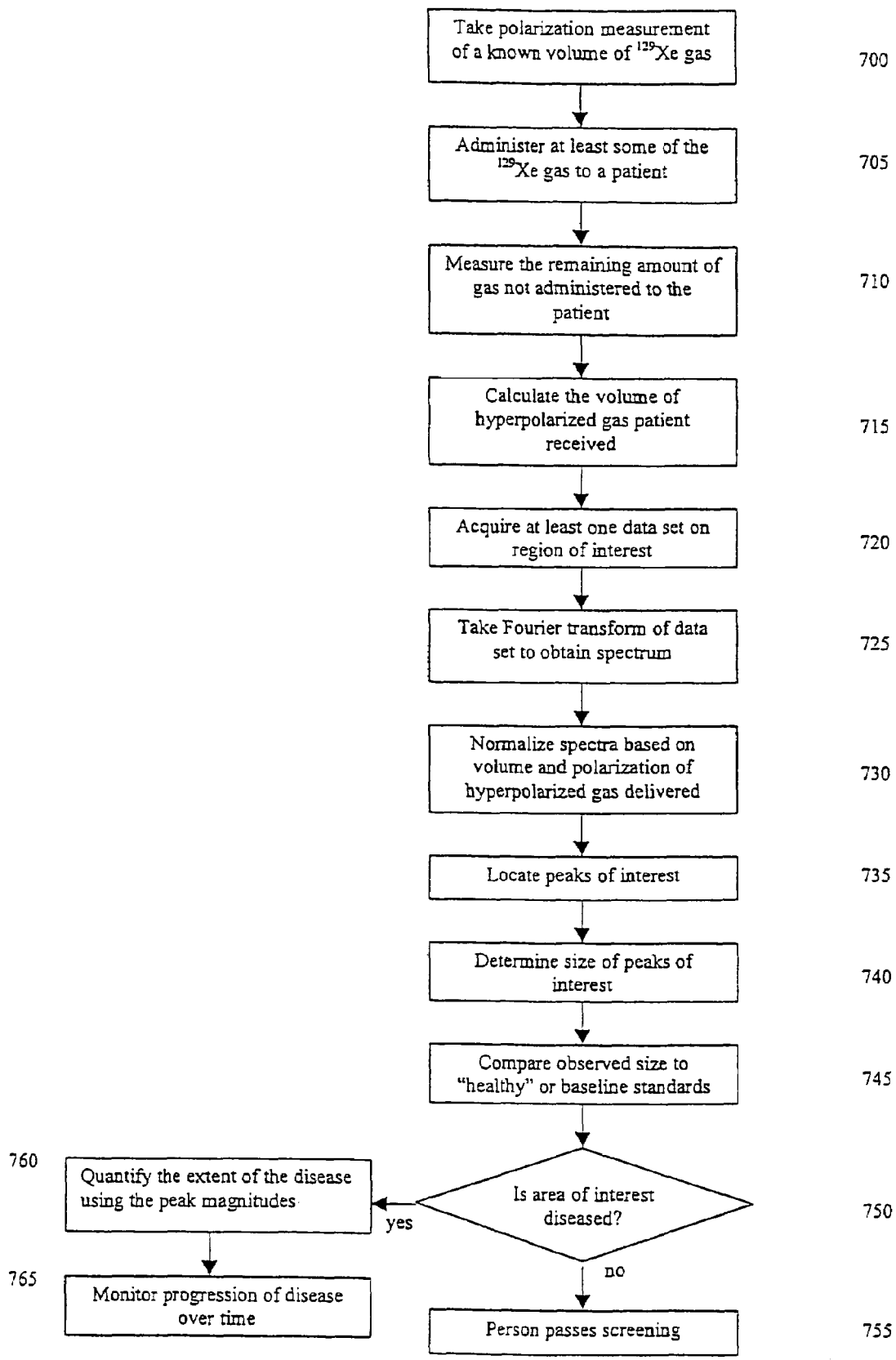
FIG. 7 is a flow chart demonstrating one method of normalizing spectra according to the present invention.

Additionally, or alternatively, another methods to normalize the data to provide reliable quantitative signal information across subjects is to factor out secondary conditions directly. For example, before administering the hyperpolarized $^{129}$Xe to a patient, the polarization (and preferably also volume) can be determined. In this scenario, "standards" for healthy populations or individuals could be established, for example, in units of signal per percent polarization per mL $^{129}$Xe administered. FIG. 7 shows one embodiment of how this technique can be used in practice. First, a polarization measurement for a known quantity of hyperpolarized gas is obtained (Block 700). Then, part or all of the measured hyperpolarized gas is administered to a patient (Block 705). The volume of gas administered to the patient is carefully measured, either automatically (as with a ventilator) or manually (such as measuring the amount remaining in the container) (Block 710). At least one data set relating to the region of interest is acquired (Block 720), and its Fourier transform calculated (Block 725). Based on the measured polarization and the volume of gas, the acquired spectra are normalized to an external standard (Block 730). The spectral peaks representing chemical shifts of interest in the resulting spectra are located (Block 735), and their size (magnitude and/or area) is determined (Block 740). A "healthy"/substantially non-diseased standard is then compared to the observed results, and if the sizes are substantially the same, the suspected ailment is not confirmed (Block 755). However, if the spectral peaks substantially differ in size, a physician or program means can quantify the extent of the disease by observing how different the observed spectral peaks are from the healthy/substantially non-diseased standard (Block 760). Preferably, if a pathological condition is suspected or confirmed, a physician will monitor the progression of the disease over time (Block 765). As mentioned hereinabove, if background subtraction is desired, preferably it is done before locating and sizing the peaks of interest (Blocks 735 and 740).

Figure 6:
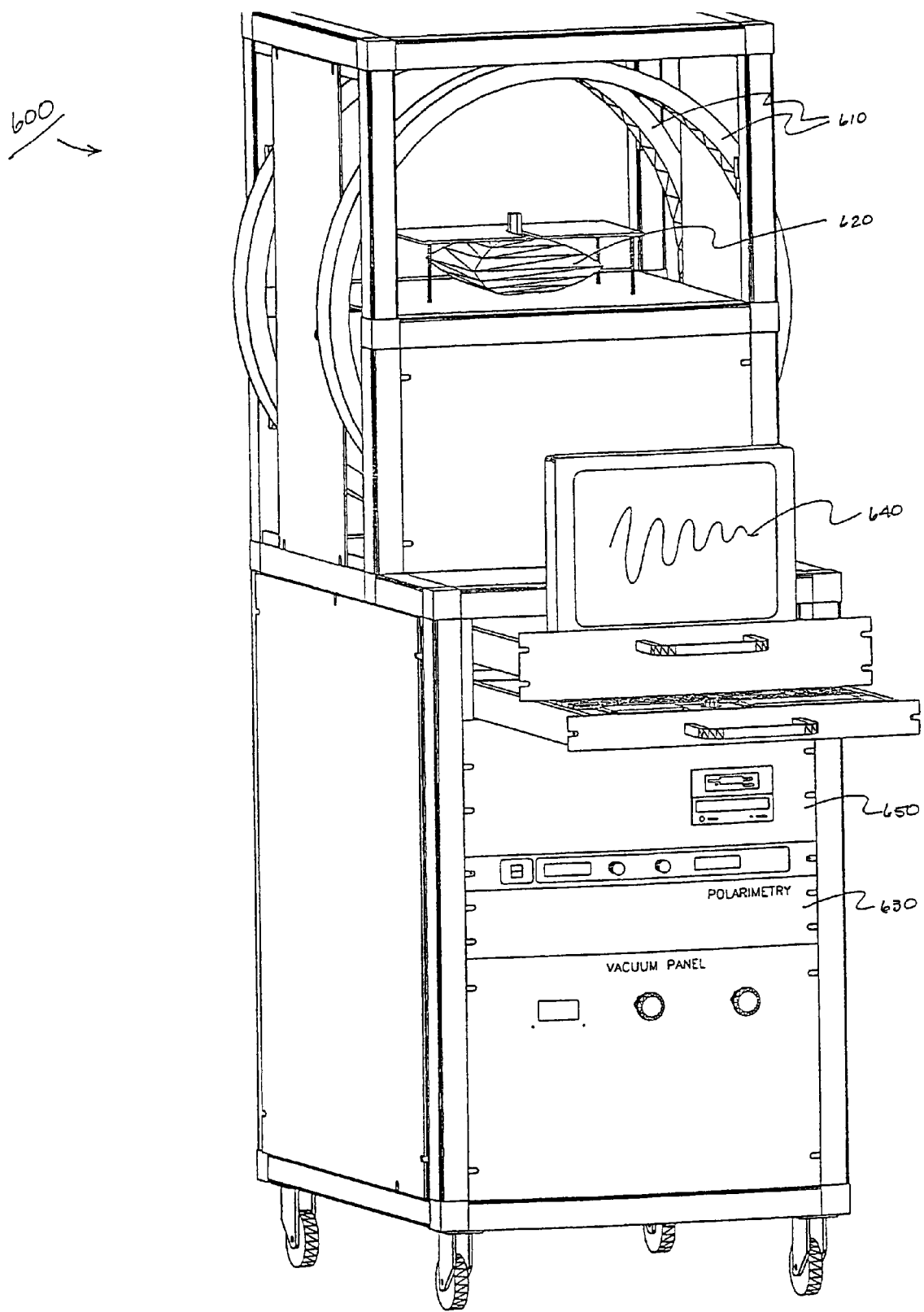
FIG. 6 is a perspective view of an apparatus for determining the extent of polarization for a sample of hyperpolarized gas.

A polarization measurement (Block 700, FIG. 7) can be obtained in an instrument such as a calibration station described in co-pending and co-assigned patent application identified by U.S. application Ser. No. 09/163,721 to Zollinger et al., entitled "Hyperpolarized Noble Gas Extraction Methods, Masking Methods, and Associated Transport Containers," the contents of which are hereby incorporated by reference as if recited in full herein. In this application, Zollinger et al. describes an apparatus for determining the extent of polarization for a sample of hyperpolarized gas (typically proximate in time but prior to administration). An apparatus 600 for evaluating the polarization as described by Zollinger et aL is shown in FIG. 6. As shown, a quantity of hyperpolarized gas 620 is placed in a magnetic field, preferably provided by a pair of Helmholtz coils 610. An NMR coil (not shown) is controlled by a circuit 630 and used to transmit an RF signal to the quantity of gas 620. The gas 620 responds to the RF signal and the NMR coil detects the response and transmits it back to the circuit 630. The response signal from the hyperpolarized gas is then processed by the circuit 630 and preferably a computer 650 and display 640. The display 640 can reflect the response of the hyperpolarized gas 620 to the RF pulse as shown in FIG. 6, or modified to display a calculated parameter such as percent polarization or the Fourier transform of the gas response (not shown). Therefore as described in Zollinger et al, the polarization extent can be accurately determined. Other methods of accurately assessing polarization are known to those of skill in the art. Preferably, a computer or program means can therefore additionally account for the initial polarization level and/or the precise volume of hyperpolarized gas administered as described hereinabove.

With the present invention as described herein, hyperpolarized $^{129}$Xe can be used as an extremely sensitive diagnostic probe for pathological conditions. More advantageously, depending on how the 129Xe is administered, the technique is either non-invasive or minimally invasive. By additional manipulation (such as subtracting a background spectrum) or by utilizing inherent properties of $^{129}$Xe in various environments, hyperpolarized $^{129}$Xe may be able to additionally allow a physician (or a computer/program means) to not only observe a biological activity of interest, but be able to clearly discern it from other activities which are not of interest. Additionally, the present invention may advantageously allow a patient to be scanned for a multitude of pathologies, possibly using a whole body coil. If a whole body coil is used, methods similar to slice-selection as known to those of skill in the art may be utilized to scan sections of a patient separately and thereby obtain data from a variety of body parts with little inconvenience to the patient.

In progressive diseases, the present invention further advantageously allows a physician to quantify the extent of a pathological condition, thereby promoting appropriate and more effective treatment. In diseases such as cancer in which metastasis occurs though the lymph system, a physician can furthermore-investigate a plurality of lymph nodes to assess the extent of the disease. Currently, multiple biopsies are carried out to investigate the status of the lymph nodes, from which a recommendation of a preferred treatment regimen (e.g. chemotherapy) is made. Utilizing hyperpolarized $^{129}$Xe to perform this interrogation could be substantially more convenient and less painful for the patient. Further advantageously, the methods of the present invention can be used to quantitatively assess the effectiveness of a treatment regimen.

Obviously, although specific pathological conditions such as Alzheimer's disease and atherosclerosis were discussed, the present invention can be used for any disease which is typically marked by a change which can be detected in vivo with hyperpolarized $^{129}$Xe NMR spectroscopic analysis, including, but not limited to, changes in cell and/or tissue composition that can be detected directly by observing chemical shifts (compared to gas phase $^{129}$Xe). In so doing, the spectroscopic analysis can be carried out based on one or more physical contrast parameters of the gas such as D, $T_1$, $T_2$, $T_2^*$, and Tip.

The following non-limiting example is provided in further description of the present invention.

EXAMPLE

Xenon-129 NMR Spectroscopy in Human Aortic Tissue

Background:

The well-established property of the $^{129}$Xe nucleus to respond to changes in the environment with a change in NMR-resonance frequency led to a proposal that the lipid-rich atherosclerotic plaques in humans could be detected by measuring the chemical shift of the xenon signal. $^{129}$Xe spectra have been recorded in human tissue at 7 T and 25 bars of pressure. The $^{129}$Xe was thermally polarized for this experiment.

Method:

Samples of aortic wall were taken from recently deceased humans, unfrozen but kept on ice. The innermost layer of the aortic wall, the intima, was dissected by lifting by tweezers and gently cutting it free with a sharp scalpel. The tissue was sliced into pieces of a few mm. Then, for each patient, a control part of "healthy" vessel wall was taken and compared to plaques cut out the same way. The plaques were scored on a graded scale ranging from 1-5 with grade 1 representing totally soft, fatty deposits, grade 3 moderate calcification, and grade 5 very hard completely mineralized deposits.

The samples were packed loosely in a heavy walled sample tube of 10 mm outer diameter and 4 mm inner diameter fitted with steel tubing and a valve. A piece of glass wool was used as a spacer to center the sample in the detection coil. The samples were pressurized with 25 bar of 80% thermally polarized $^{129}$Xe (remainder other Xe isotopes) without freezing. The sample tube was then transferred to an NMR spectrometer and $^{129}$Xe spectra were recorded at 7 T at a resonance frequency of 82.98 MHz and at a temperature of 37° C. The chemical shifts are given in ppm with the $^{129}$Xe gas peak set to 0 ppm.

Results:

The significant results are summarized in Table 3 below. The conclusion is that there is a difference in chemical shift of slightly less than 2 ppm (1.5-1.9), which can be deemed significant in a spectrometer of the quality used in this study.

TABLE 3

| Sample no. | Age | Sex | Cause of death | Plaque, grade | Healthy (ppm) | Plaque (ppm) | Difference (ppm) |
|---|---|---|---|---|---|---|---|
| 1 | 70 | F | Suffocation | 2-3 | 187.4 | 188.9 | 1.5 |
| 2 | 55 | M | Cardiac infarct | 4-5 | 189.2 | 187.29 | 1.9 |

It is anticipated that for in vivo applications, the signal can be obtained, enhanced or optimized by certain of the techniques described above to help amplify the chemical shift associated with the pathological condition of interest. That is, the signal strength can be influenced by the degree of polarization of the $^{129}$Xe at administration, the time it takes the polarized gas product to reach the region of interest for the pathology under evaluation, and how much of the polarization/gas is taken up by the pathology under evaluation, and the selected pulse sequence and timing thereof (relative to administration of the polarized gas). For example, the pulse sequence can be adjusted to suppress or enhance the desired spectra in the response signal such as by selecting a weighted $T_2$ or delayed $T_1$ contrast parameter. For a particular, condition, a line shape, peak amplitude, area under the peak or peaks of interest, peak-to-peak ratio (or ratio of the area under those peaks), or other desired value at one or more chemical shift regions may be representative of the disease. For example, for atherosclerotic plaque, if the plaque is at a stage where it is lipid rich with (fatty unstable) lesions, the signal may be increased (and centered over a different chemical shift location) over late stage hardened plaque.

In the results presented above, the chemical shift is up (from 187.4 to 188.9) for the female sample and down (from 189.2 to 187.29) for the male sample. This shift variation may be attributed to the plaque grade, or may be associated with gender and/or age. It is also possible that the "healthy tissue" was at an earlier stage of the disease, but perhaps not without some plaque. Another variable to consider in the data obtained in this study is the possibility in the variation of pressure in the volume of the vessel/tissue on the signal for the samples. In addition, when comparing to the discussion for FIG. 10, the location of the signal spectra location in this study should be adjusted up by about 11 ppm to account for the increase in pressure. That is, high pressures shift the gas resonance. Thus, for sample no. 1, the plaque ppm at 188.9 generally corresponds to a 199.9 ppm.

Figure 12A:
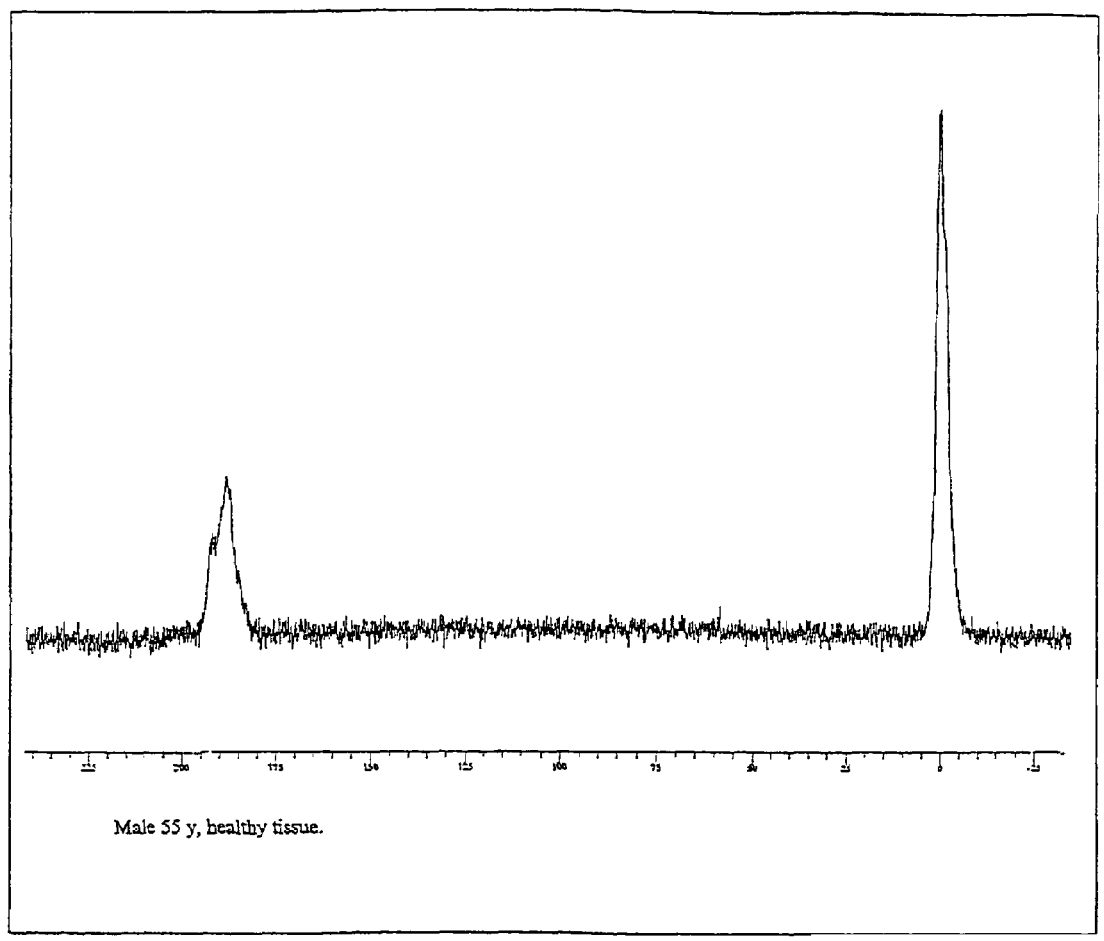
FIGS. 12A and 12B are graphs of a spectrum of an NMR signal of an in vitro sample of an aortic wall of a 55 year-old deceased human male exposed to thermally polarized $^{129}$Xe at 25 bars of pressure.
Figure 12B:
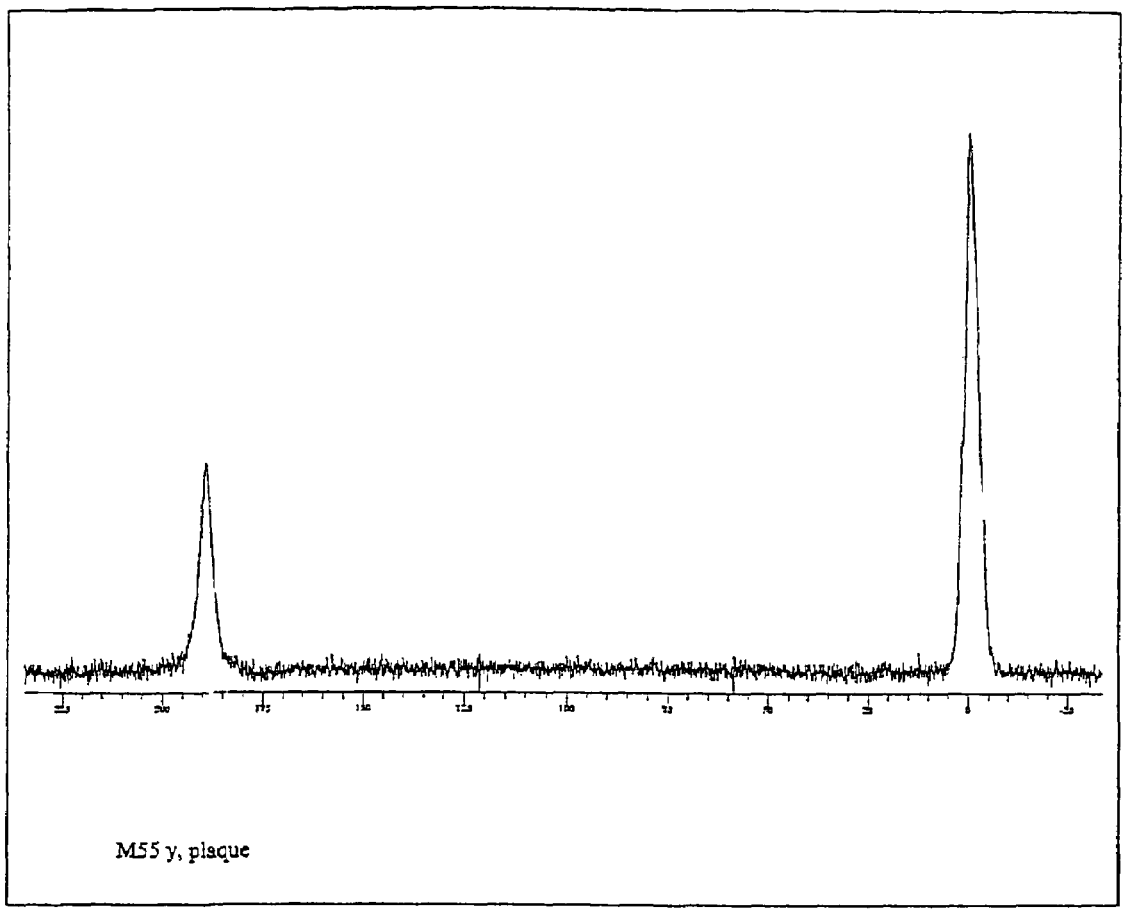
Figure 13A:
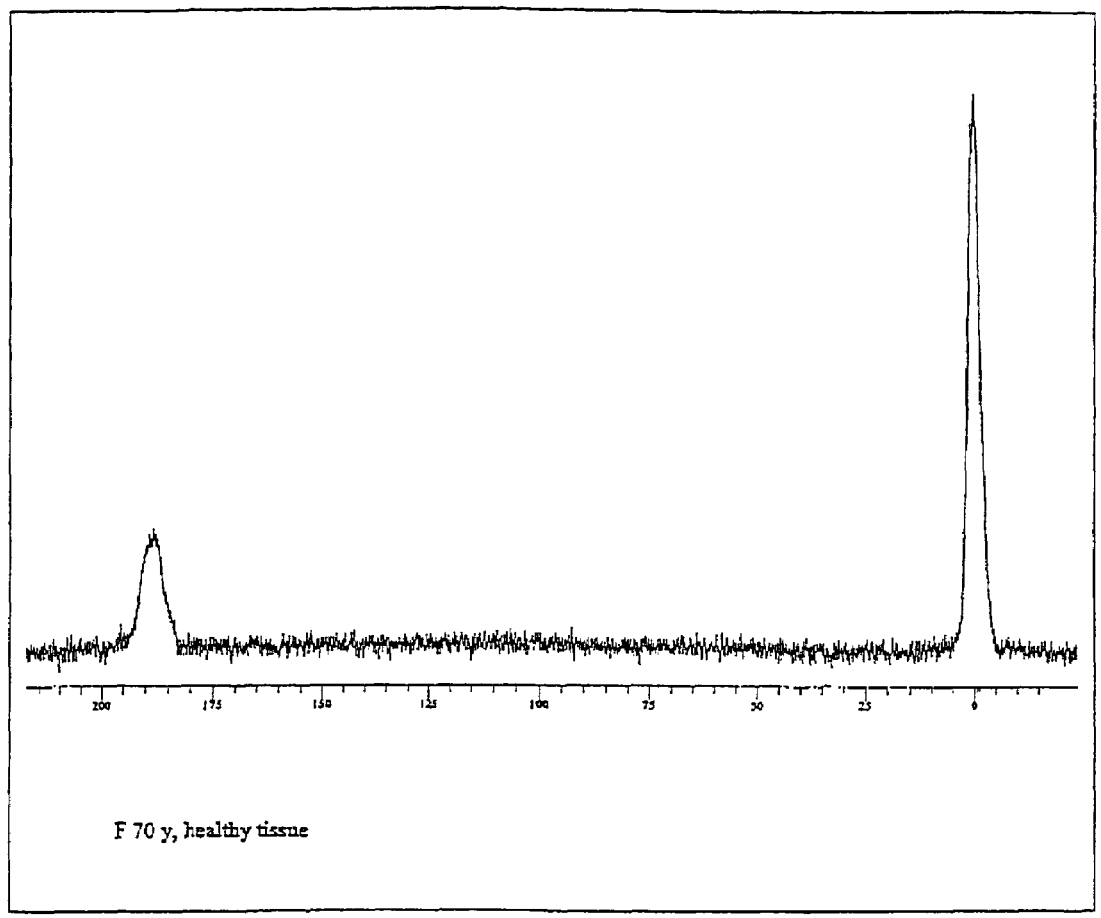
FIGS. 13A and 13B are graphs of a spectrum of an NMR signal of an in vitro sample of an aortic wall of a 70 year-old deceased human female exposed to thermally polarized $^{129}$Xe at 25 bars of pressure.
Figure 13B:
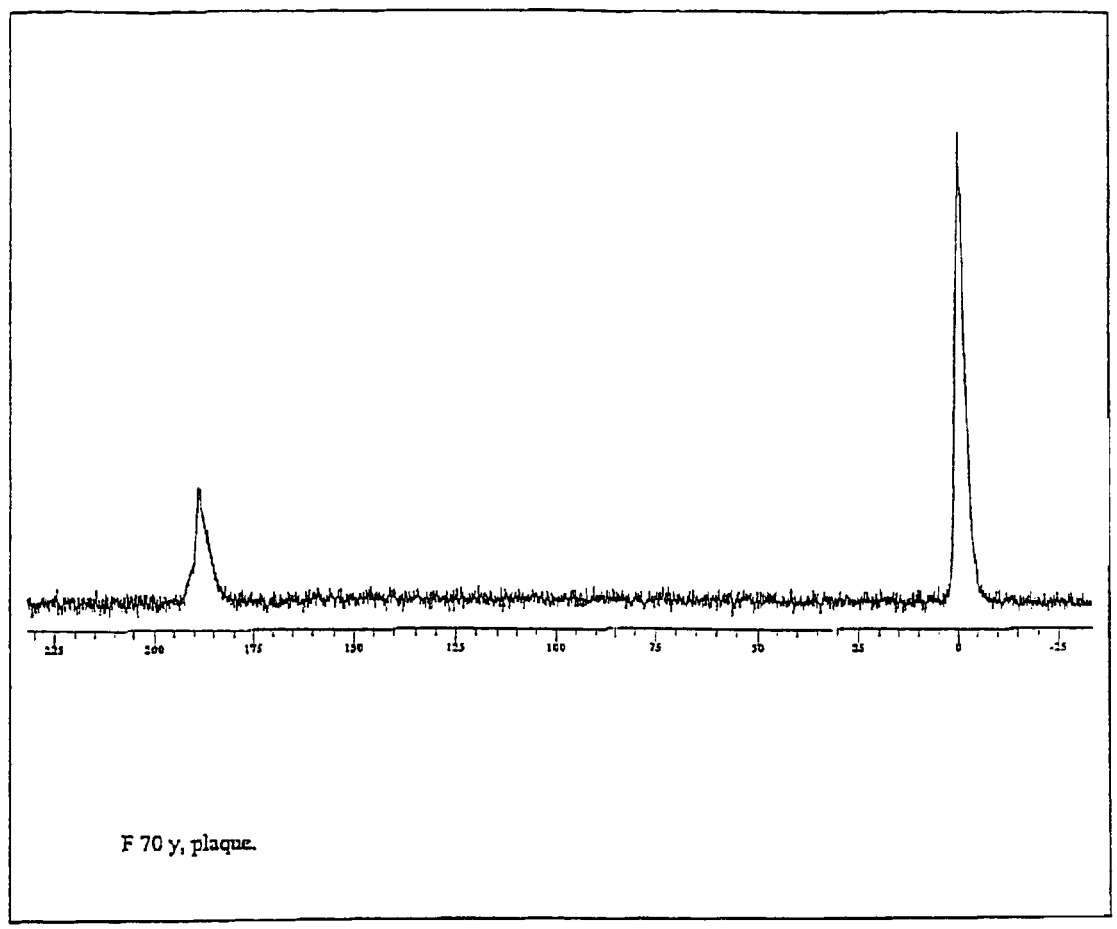

FIGS. 12A and 12B illustrate the spectrum for the male samples discussed above. The chemical peak for the tissue of interest illustrates that not only is there a detectable shift, the line shape and/or peak(s) may also be different (one peak present in either the "normal" or "healthy" tissue may be reduced, shifted, or absent in the other tissue). These differences can be analyzed by statistical curve fitting algorithms known to those of skill in the art. FIGS. 13A and 13B illustrate a similar alteration in line shape, shift, and peak magnitude, for the female samples.

The foregoing is illustrative of the present invention and is not to be construed as limiting thereof. Although a few exemplary embodiments of this invention have been described, those skilled in the art will readily appreciate that many modifications are possible to the exemplary embodiments without materially departing from the novel teachings and advantages of this invention. Accordingly, all such modifications are intended to be included within the scope of this invention as defined in the claims. In the claims, means-plus-function clause are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

What is claimed is:

1. A method for detecting atherosclerosis suitable for in vivo evaluations comprising:

administering a first bolus of hyperpolarized $^{129}$Xe gas in vivo to a patient so that said hyperpolarized $^{129}$Xe travels to a region of interest;

applying a first at least one excitation pulse to said first administered hyperpolarized $^{129}$Xe in the region of interest;

acquiring at least one first response signal spectrum presenting a response of said hyperpolarized $^{129}$Xe to said at least one pulse via nuclear magnetic resonance spectroscopy;

identifying at least one spectral region of interest in said first response signal spectrum;

analyzing said at least one spectral region of interest in said first response signal spectrum;

determining the presence of atherosclerotic plaques on the basis of the presence or absence of at least one spectral peak and/or at lest one selected feature of at least one spectral peak in the response signal spectrum based on said analyzing and identifying steps;

providing a therapeutic agent to the patient to treat the atherosclerotic condition; then administering a second bolus of hyperpolarized $^{129}$Xe gas in vivo to a patient so that said hyperpolarized $^{129}$Xe travels to a region of interest;

applying a second at least one excitation pulse to said second administered hyperpolarized $^{129}$Xe in the region of interest;

acquiring at least one second response signal spectrum representing the response of said hyperpolarized $^{129}$Xe to said at least one pulse sequence via nuclear magnetic resonance spectroscopy;

identifying at least one spectral region of interest ins aid second response signal spectrum;

analyzing said at least one spectral region of interest in said second response signal; and evaluating the treatment efficacy of the therapeutic agent based on the first and second analyzing steps.

2. A method according to claim 1, wherein said evaluating step comprises comparing selected spectral characteristics in the first and second response signal spectrums.

3. A method according to claim 1, wherein said second analyzing step further comprises identifying whether the atherosclerotic condition has deteriorated or progressed from the time of the first analyzing step.

4. A method according to claim 1, further comprising evaluating at least one of the acquired first and second response signal spectrums to identify whether the atherosclerosis is likely to correspond to an early stage with soft, fatty deposits, an intermediate stage with moderate calcification, or a late stage with hard mineralized or calcified deposits and/or lesions.

5. A method for detecting atherosclerosis according to claim 1, wherein the region of interest comprises at least one of the carotid arteries.

6. A method for detecting atherosclerosis according to claim 5, wherein said at least one excitation pulse for the first and second applying steps comprises a resonant RF pulse sequence selected to produce large flip angles in said hyperpolarized $^{129}$Xe.

7. A method according to claim 1, wherein the first applying, acquiring and analyzing steps are carried out to define a baseline physiological profile of the patient.

8. A method according to claim 1, wherein at least said first analyzing step comprises assessing whether the width of a curve associated with a peak in the response spectrum is narrower than a corresponding peak in a reference spectrum corresponding to an epidemiological study and/or an a priori baseline spectrum to determine whether the patient has atherosclerosis.

* * * * *